(12) United States Patent
Peeters et al.

(10) Patent No.: US 8,948,935 B1
(45) Date of Patent: Feb. 3, 2015

(54) PROVIDING A MEDICAL SUPPORT DEVICE VIA AN UNMANNED AERIAL VEHICLE

(71) Applicant: Google Inc., Mountain View, CA (US)

(72) Inventors: Eric Peeters, Mountain View, CA (US); Eric Teller, Palo Alto, CA (US); William Graham Patrick, San Francisco, CA (US); Sergey Brin, Palo Alto, CA (US)

(73) Assignee: Google Inc., Mountain View, CA (US)

( * ) Notice: Subject to any disclaimer, the term of this patent is extended or adjusted under 35 U.S.C. 154(b) by 36 days.

(21) Appl. No.: 13/732,958

(22) Filed: Jan. 2, 2013

(51) Int. Cl.
*G06Q 10/00* (2012.01)
*B64C 39/02* (2006.01)

(52) U.S. Cl.
CPC ...................................... *B64C 39/02* (2013.01)
USPC ................................................ 701/3; 709/201

(58) Field of Classification Search
USPC ................................................ 701/3; 709/201
See application file for complete search history.

(56) References Cited

U.S. PATENT DOCUMENTS

| | | | |
|---|---|---|---|
| 6,056,237 A | 5/2000 | Woodland | |
| 6,567,044 B2 | 5/2003 | Carroll | |
| 6,817,573 B2 | 11/2004 | Harrison et al. | |
| 6,965,816 B2 | 11/2005 | Walker | |
| 7,574,193 B2 | 8/2009 | Hulkkonen et al. | |
| 7,813,888 B2 | 10/2010 | Vian et al. | |
| 7,877,785 B2 | 1/2011 | Selignan | |
| 8,028,952 B2 | 10/2011 | Urnes, Sr. | |
| 2007/0049251 A1 | 3/2007 | Mock et al. | |
| 2008/0085732 A1 | 4/2008 | Mizuide et al. | |
| 2010/0084513 A1 | 4/2010 | Gariepy et al. | |
| 2010/0168949 A1* | 7/2010 | Malecki et al. | .................. 701/24 |
| 2010/0243815 A1* | 9/2010 | Wong et al. | ................. 244/137.4 |
| 2010/0256839 A1 | 10/2010 | Fitzpatrick | |
| 2010/0280699 A1 | 11/2010 | Bageshwar et al. | |
| 2011/0084162 A1 | 4/2011 | Goossen et al. | |
| 2011/0128372 A1 | 6/2011 | Malecki et al. | |
| 2011/0130636 A1* | 6/2011 | Daniel et al. | .................. 600/301 |
| 2011/0267241 A1 | 11/2011 | Grimm et al. | |
| 2011/0281679 A1 | 11/2011 | Larrabee et al. | |
| 2011/0315806 A1 | 12/2011 | Piasecki et al. | |
| 2012/0080556 A1 | 4/2012 | Root, Jr. | |

(Continued)

OTHER PUBLICATIONS

Mitchell J.H. Lum, et al, Telesurgery Via Unmanned Aerial Vehicle (UAV) with a Field Deployable Surgical Robot, Medicine Meets Virtual Reality 15, Feb. 2007, Long Beach, California.

H.S. Nguyen, et al., Situation Identification by Unmanned Aerial Vehicle, Institute of Mathematics, 2001, pp. 49-56, Warsaw University.

(Continued)

*Primary Examiner* — Mary Cheung
*Assistant Examiner* — Yuen Wong
(74) *Attorney, Agent, or Firm* — McDonnell Boehnen Hulbert & Berghoff LLP

(57) ABSTRACT

Embodiments described herein may relate to an unmanned aerial vehicle (UAV) navigating to a medical situation in order to provide medical support. An illustrative method involves a UAV (a) housing a medical-support device, (b) determining a target location associated with at least one individual in need of medical assistance, (c) navigating the UAV from a remote location to the target location, (d) the computing system making a determination that the UAV is located at the target location, and (e) in response to the determination that the UAV is located at the target location, delivering by a delivery mechanism the medical-support device for providing medical assistance for the at least one individual in need of medical assistance.

25 Claims, 14 Drawing Sheets

(56) References Cited

U.S. PATENT DOCUMENTS

2012/0123628 A1* 5/2012 Duggan et al. ................ 701/24
2012/0152654 A1  6/2012 Marcus

OTHER PUBLICATIONS

Elizabeth Bone et al., Unmanned Aerial Vehicles: Background and Issues for Congress, Report for Congress, Congressional Research Service, The Library of Congress, Apr. 25, 2003.

* cited by examiner

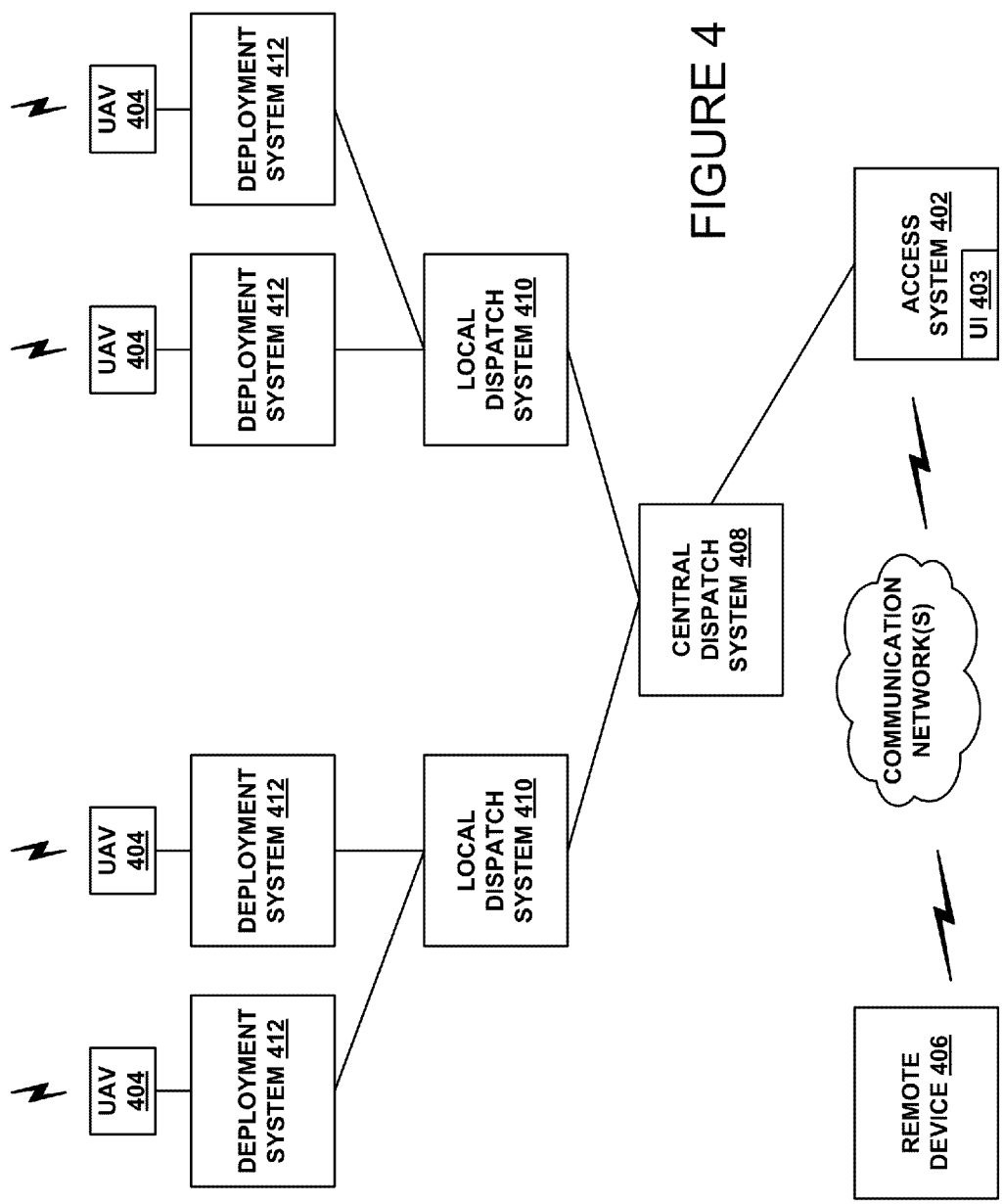

PROVIDING A MEDICAL SUPPORT DEVICE VIA AN UNMANNED AERIAL VEHICLE

BACKGROUND

Unless otherwise indicated herein, the materials described in this section are not prior art to the claims in this application and are not admitted to be prior art by inclusion in this section.

An unmanned vehicle, which may also be referred to as an autonomous vehicle, is a vehicle capable of travel without a physically-present human operator. An unmanned vehicle may operate in a remote-control mode, in an autonomous mode, or in a partially autonomous mode.

When an unmanned vehicle operates in a remote-control mode, a pilot or driver that is at a remote location can control the unmanned vehicle via commands that are sent to the unmanned vehicle via a wireless link. When the unmanned vehicle operates in autonomous mode, the unmanned vehicle typically moves based on pre-programmed navigation waypoints, dynamic automation systems, or a combination of these. Further, some unmanned vehicles can operate in both a remote-control mode and an autonomous mode, and in some instances may do so simultaneously. For instance, a remote pilot or driver may wish to leave navigation to an autonomous system while performing another task such as operating a mechanical system for picking up objects via remote control.

Various types of unmanned vehicles exist for various different environments. For example, unmanned vehicles exist for operation in the air, on the ground, underwater, and in space. Unmanned vehicles also exist for hybrid operations in which multi-environment use is possible. Examples of hybrid unmanned vehicles include an amphibious craft that is capable of operation on land as well as on water or a floatplane that is capable of landing on water as well as on land.

SUMMARY

In one aspect, an unmanned aerial vehicle (UAV) may include: (i) a housing that is configured to hold a medical-support device; (ii) a delivery mechanism that is configured to deliver the medical-support device to a target location associated with at least one individual in need of medical assistance; and (iii) a control system configured to: (a) determine the target location; (b) navigate the UAV from a remote location to the target location; (c) make a determination that the UAV is located at the target location; and (d) in response to the determination that the UAV is located at the target location, cause the delivery mechanism to deliver the medical-support device at the target location for providing medical assistance for the at least one individual in need of medical assistance.

In another aspect, an example method may involve: (i) housing, by a housing system of a UAV, a medical-support device; (ii) determining, by a computing system of the UAV, a target location associated with at least one individual in need of medical assistance; (iii) the computing system navigating the UAV from a remote location to the target location; (iv) the computing system making a determination that the UAV is located at the target location; and (v) in response to the determination that the UAV is located at the target location, delivering, by a delivery mechanism, the medical-support device for providing medical assistance for the at least one individual in need of medical assistance.

In a further aspect, a non-transitory computer readable medium may have stored therein instructions that are executable to cause a computing system to perform functions including: (i) determining a target location associated with at least one individual in need of medical assistance; (ii) using a navigation system to navigate the UAV from a remote location to the target location; (iii) making a determination that the UAV is located at the target location; and (iv) in response to the determination that the UAV is located at the target location associated with the at least one individual in need of medical assistance, delivering, by a delivery mechanism, the medical-support device for providing medical assistance to the at least one individual in need of medical assistance.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 4 is a simplified block diagram illustrating a medical support system, according to an example embodiment.

DETAILED DESCRIPTION

Figure 1:
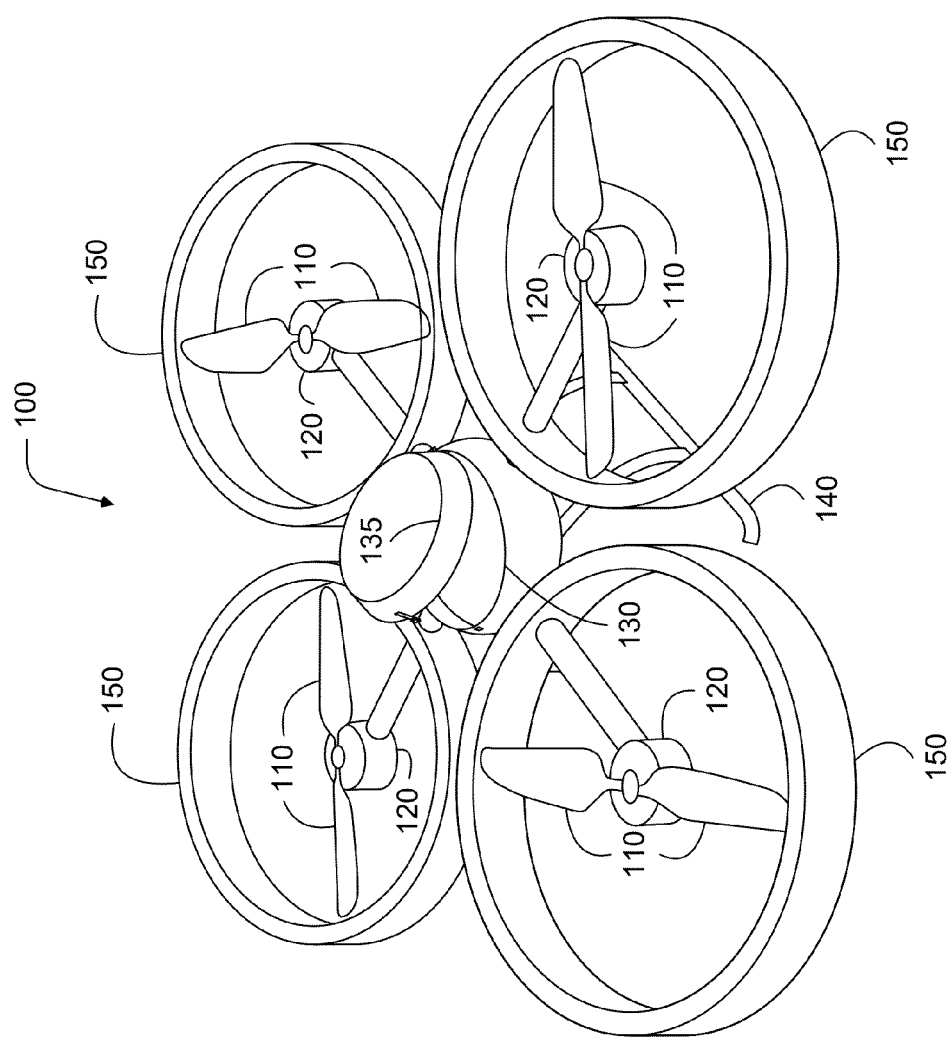
FIGS. 1, 2, 3A and 3B are simplified illustrations of unmanned aerial vehicles, according to example embodiments.

Exemplary methods and systems are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

I. OVERVIEW

Embodiments described herein may relate to and/or may be implemented in a system in which unmanned vehicles, and in particular, "unmanned aerial vehicles" (UAVs), are configured to provide medical support.

In an illustrative embodiment, a medical-support system may include a fleet of UAVs that are distributed throughout a geographic area, such as a city. The medical-support system may be configured for communications with remote devices, such as mobile phones, so that medical support can be requested by a person in need of such medical support (or by others on behalf of a person in need). The medical-support system can then dispatch the appropriate UAV or UAVs to the scene of the medical situation in order to provide medical support.

In particular, a medical-support system may include a fleet with a number of different types of UAVs, which are configured for different medical situations. For instance, some UAVs may be configured with items and/or functionality that are expected to be helpful in a cardiac-arrest situation, some UAVs may be configured to help a choking victim, some UAVs may be configured to help a trauma victim, and so on. As such, an illustrative medical-support system may be configured to identify or classify the particular type of medical situation that is occurring, to select the appropriate UAV from those that are available, and to dispatch the selected UAV to the scene of the medical situation.

In a further aspect, a UAV may be configured to transport a medical-support device to a remote location where a medical situation is occurring or has occurred. In particular, the UAV can carry or house the medical-support device in such a way that it may be delivered to the location of the medical situation. Further, due to their size and maneuverability, UAVs may be able to reach the scene of a medical situation and provide medical support more quickly than traditional emergency response vehicles, such as an ambulance, fire truck, or police car.

In an example embodiment, a UAV can transport a medical-support device that is associated with the type of medical situation that occurred or is occurring. For example, items that may aid in diagnosing and/or treating a person who needs medical assistance, or may serve other purposes, may be delivered. Such items may include, but are not limited to: (a) medicines, (b) diagnostic devices, such as a pulse oximeter, blood pressure sensor, or EKG sensor, (c) treatment devices, such as an epinephrine injection, a first aid kit, or a defibrillator, and/or (d) remote support devices, such as a mobile phone or a head-mountable device (HMD), among other possibilities.

As a specific example, a UAV may include a compartment that houses a defibrillator, and be configured to fly the defibrillator from a remote location to a person who has just suffered from cardiac arrest. By doing so, the defibrillator may be delivered and used to treat the person more quickly than if it had been carried to the scene by an ambulance or fire truck, for example.

As another specific example, a UAV may have a compartment that holds a head-mountable device (HMD) that is preloaded with or otherwise able to provide video instructions for administering a medical treatment or procedure, such as a video tutorial describing how to perform cardiopulmonary resuscitation (CPR), for example. The UAV may fly to the scene of a medical situation, where a bystander may remove the HMD from the UAV and wear the HMD. As such, the bystander may be provided with instructions as to how to perform the medical procedure. This may allow the medical procedure to be administered more quickly than if a victim had to wait for an emergency medical technician or paramedic to arrive at the scene.

As a further example, instructions for the medical procedures may be provided through the use of augmented reality technology. For example, instructions may be overlaid on the body of the person in need of medical assistance thus allowing a bystander to visually follow the augmented reality. In one example, augmented reality may include instructions in the form of a visual overlay illustrating where to push on an individual's chest in order to properly perform CPR. In another example, the augmented reality may provide a visual overlay illustrating where to attach AED electrodes. Other examples of augmented reality signals may exist as well. The medical-support devices that are delivered by the UAV, such as an HMD, may provide these instructions. Alternatively, these instructions may be supplied through the use of a display or projector from the UAV itself.

Additionally, the UAV may be implemented with telemedicine capabilities in order to provide medical support. For example, the UAV may deliver devices that contain input and output technology such that they can communicate with a remote location. These communications may occur through the use of an HMD, such as using a camera and microphone on the HMD to relay information to the remote location and allow medical personnel to provide medical assistance. Alternatively, the UAV itself may communicate with a remote location, such that video and audio information related to the medical situation may be sent to the remote location. Likewise, the remote location may send information to the UAV located at the medical situation. The UAV may thus be equipped with speakers, microphones, or other communication devices that allow communication with the remote location.

In the above and other examples, a UAV may include a control system that determines a target location that is associated with a medical situation. The control system may navigate the UAV from a remote location to the target location. Once the control system recognizes that the UAV has reached the target location, the medical-support device may be delivered to the medical situation. Alternatively, the UAV may be operated by a remote device.

In order to deliver the medical-support device, the UAV may implement various carrying methods. For example, the UAV may carry the medical-support device in a compartment of the UAV. The size and shape of the compartment may depend on the configuration of the medical-support device being delivered. Additionally, the compartment may be configured for temperature control and provide a power source such that the medical-support device may be delivered in a functioning state. In another embodiment, the UAV may use a pick-and-place mechanism to deliver the medical-support device, which is configured to pick up and hold the device while the UAV is in flight. Other examples may be possible as well.

In yet a further aspect, the UAV may use different methods to deliver the medical-support device. In one embodiment, the UAV may land at the target location such that the individual or individuals at the scene of the medical situation may unload the device from the compartment. In another embodiment, the device my slide out of the compartment in response to a command from the UAV. Alternatively, the UAV may hover over the target location and release the medical-support device such that it drops to the ground or parachutes downward. Other examples may also be possible.

Herein, a "medical situation" should be understood to include any situation to which government or private entity, such as a police department, a fire department, and/or an emergency medical services (EMS) entity, might dispatch its personnel. Therefore, some medical situations may in fact be non-medical in nature. For example, an emergency situation to which a police car, fire truck, or ambulance might be dispatched may be considered a medical situation for purposes of this disclosure. Medical support may not be required at such emergency situations (e.g., when police are sent to the scene of a non-violent crime). Further, some non-emergency situations to which a police car, fire truck, ambulance, or the like might be dispatched, may also be considered a medical situation for purposes of this disclosure. Thus, while exemplary embodiments may be described as being implemented to help provide medical support at the scene of a medical situation, those skilled in the art will understand that the UAVs, the functionality of such UAVs, and/or other aspects of the embodiments that are explicitly described herein can also apply in non-medical and/or non-emergency applications.

It should be understood that the above embodiments, and other embodiments described herein, are provided for explanatory purposes, and are not intended to be limiting.

II. ILLUSTRATIVE AUTONOMOUS VEHICLES

The term "unmanned aerial vehicle," as used in this disclosure, refers to any autonomous or semi-autonomous vehicle that is capable of performing some functions without a physically-present human pilot. Examples of flight-related functions may include, but are not limited to, sensing its environment or operating in the air without a need for input from an operator, among others.

A UAV may be autonomous or semi-autonomous. For instance, some functions could be controlled by a remote human operator, while other functions are carried out autonomously. Further, a UAV may be configured to allow a remote operator to take over functions that can otherwise be controlled autonomously by the UAV. Yet further, a given type of function may be controlled remotely at one level of abstraction and performed autonomously at another level of abstraction. For example, a remote operator could control high level navigation decisions for a UAV, such as by specifying that the UAV should travel from one location to another (e.g., from the city hall in Palo Alto to the city hall in San Francisco), while the UAV's navigation system autonomously controls more fine-grained navigation decisions, such as the specific route to take between the two locations, specific flight controls to achieve the route and avoid obstacles while navigating the route, and so on. Other examples are also possible.

A UAV can be of various forms. For example, a UAV may take the form of a rotorcraft such as a helicopter or multicopter, a fixed-wing aircraft, a jet aircraft, a ducted fan aircraft, a lighter-than-air dirigible such as a blimp or steerable balloon, a tail-sitter aircraft, a glider aircraft, and/or an ornithopter, among other possibilities. Further, the terms "drone", "unmanned aerial vehicle system" ("UAVS"), or "unmanned aerial system" ("UAS") may also be used to refer to a UAV.

FIG. 1 is a simplified illustration of a UAV, according to an example embodiment. In particular, FIG. 1 shows an example of a rotorcraft 100 that is commonly referred to as a multi-copter. Multicopter 100 may also be referred to as a quadcopter, as it includes four rotors 110. It should be understood that example embodiments may involve rotorcraft with more or less rotors than multicopter 100. For example, a helicopter typically has two rotors. Other examples with three or more rotors are possible as well. Herein, the term "multicopter" refers to any rotorcraft having more than two rotors, and the term "helicopter" refers to rotorcraft having two rotors.

Referring to multicopter 100 in greater detail, the four rotors 110 provide propulsion and maneuverability for the multicopter 100. More specifically, each rotor 110 includes blades that are attached to a motor 120. Configured as such the rotors may allow the multicopter 100 to take off and land vertically, to maneuver in any direction, and/or to hover. Furthermore, the pitch of the blades may be adjusted as a group and/or differentially, and may allow a multicopter 110 to perform three-dimensional aerial maneuvers such as an upside-down hover, a continuous tail-down "tic-toc," loops, loops with pirouettes, stall-turns with pirouette, knife-edge, immelmann, slapper, and traveling flips, among others. When the pitch of all blades is adjusted to perform such aerial maneuvering, this may be referred to as adjusting the "collective pitch" of the multicopter 100. Blade-pitch adjustment may be particularly useful for rotorcraft with substantial inertia in the rotors and/or drive train, but is not limited to such rotorcraft Additionally or alternatively, multicopter 100 may propel and maneuver itself by adjusting the rotation rate of the motors, collectively or differentially. This technique may be particularly useful for small electric rotorcraft with low inertia in the motors and/or rotor system, but is not limited to such rotorcraft.

Multicopter 100 also includes a central enclosure 130 with a hinged lid 135. The central enclosure may contain, e.g., control electronics such as an inertial measurement unit (IMU) and/or an electronic speed controller, batteries, other sensors, and/or a payload, among other possibilities.

The illustrative multicopter 100 also includes landing gear 140 to assist with controlled take-offs and landings. In other embodiments, multicopters and other types of UAVs without landing gear are also possible.

In a further aspect, multicopter 100 includes rotor protectors 150. Such rotor protectors 150 can serve multiple purposes, such as protecting the rotors 110 from damage if the multicopter 100 strays too close to an object, protecting the multicopter 100 structure from damage, and protecting nearby objects from being damaged by the rotors 110. It should be understood that in other embodiments, multicopters and other types of UAVs without rotor protectors are also possible. Further, rotor protectors of different shapes, sizes, and function are possible, without departing from the scope of the invention.

Figure 2:
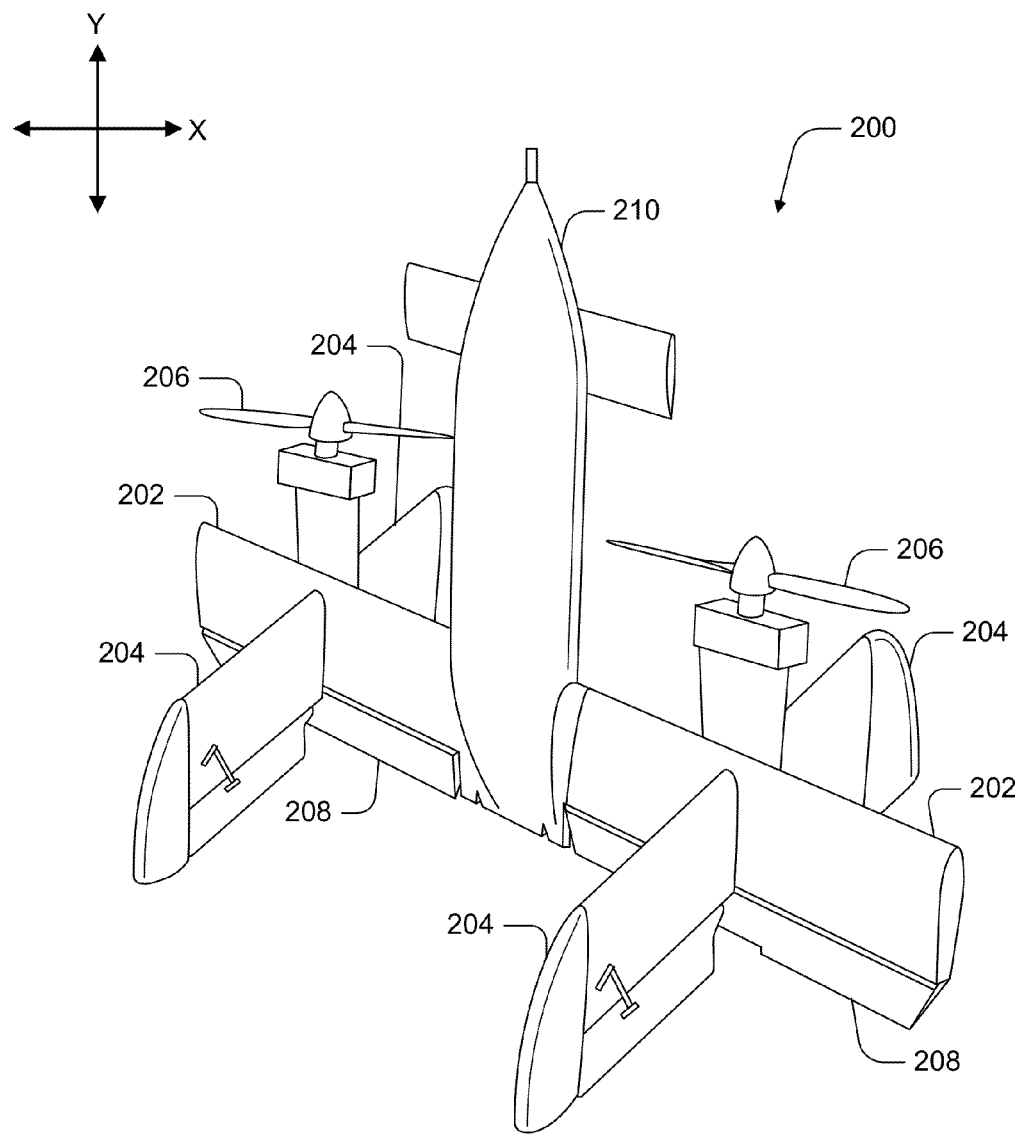

A multicopter 100 may control the direction and/or speed of its movement by controlling its pitch, roll, yaw, and/or altitude. To do so, multicopter 100 may increase or decrease the speeds at which the rotors 110 spin. For example, by maintaining a constant speed of three rotors 110 and decreasing the speed of a fourth rotor, the multicopter 100 can roll right, roll left, pitch forward, or pitch backward, depending upon which motor has its speed decreased. Specifically, the multicopter may roll in the direction of the motor with the decreased speed. As another example, increasing or decreasing the speed of all rotors 110 simultaneously can result in the multicopter 100 increasing or decreasing its altitude, respectively. As yet another example, increasing or decreasing the speed of rotors 110 that are turning in the same direction can result in the multicopter 100 performing a yaw-left or yaw-right movement. These are but a few examples of the different types of movement that can be accomplished by independently or collectively adjusting the RPM and/or the direction that rotors 110 are spinning FIG. 2 is a simplified illustration of a UAV, according to an example embodiment. In particular, FIG. 2 shows an example of a tail-sitter UAV 200. In the illustrated example, the tail-sitter UAV 200 has fixed wings 202 to provide lift and allow the UAV to glide horizontally (e.g., along the x-axis, in a position that is approximately perpendicular to the position shown in FIG. 2). However, the fixed wings 202 also allow the tail-sitter UAV 200 to take off and land vertically on its own.

For example, at a launch site, tail-sitter UAV 200 may be positioned vertically (as shown) with fins 204 and/or wings 202 resting on the ground and stabilizing the UAV in the vertical position. The tail-sitter UAV 200 may then take off by operating propellers 206 to generate the upward thrust (e.g., a thrust that is generally along the y-axis). Once at a suitable altitude, the tail-sitter UAV 200 may use its flaps 208 to reorient itself in a horizontal position, such that the fuselage 210 is closer to being aligned with the x-axis than the y-axis. Positioned horizontally, the propellers 206 may provide forward thrust so that the tail-sitter UAV 200 can fly in a similar manner as a typical airplane.

Variations on the illustrated tail-sitter UAV 200 are possible. For instance, tail-sitter UAVs with more or less propellers, or that utilize a ducted fan or multiple ducted fans, are also possible. Further, different wing configurations with more wings (e.g., an "x-wing" configuration with four wings), with less wings, or even with no wings, are also possible. More generally, it should be understood that other types of tail-sitter UAVs and variations on the illustrated tail-sitter UAV 200 are also possible.

As noted above, some embodiments may involve other types of UAVs, in addition or in the alternative to multicopters. For instance, FIGS. 3A and 3B are simplified illustrations of other types of UAVs, according to example embodiments.

Figure 3A:
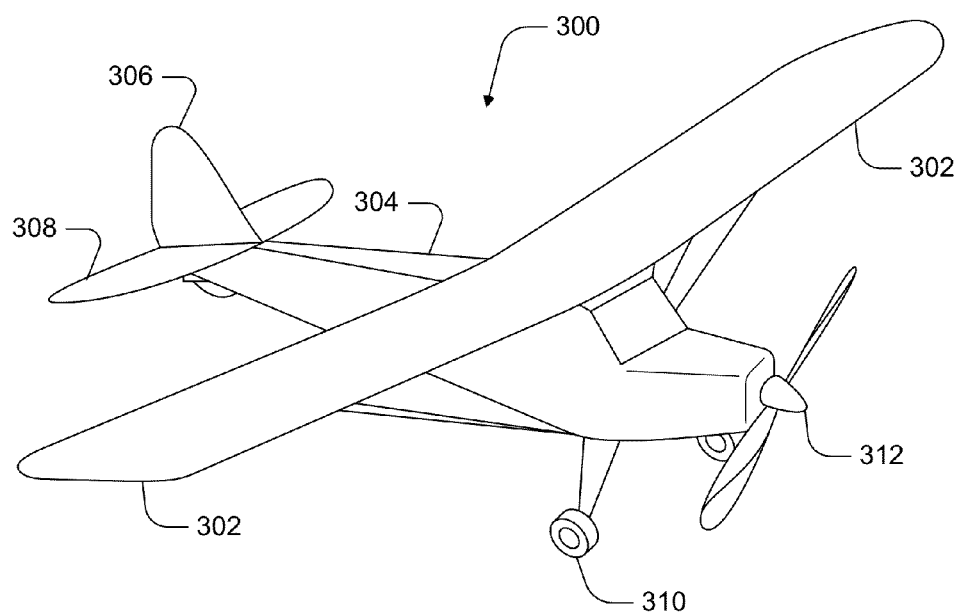

In particular, FIG. 3A shows an example of a fixed-wing aircraft 300, which may also be referred to as an airplane, an aeroplane, or simply a plane. A fixed-wing aircraft 300, as the name implies, has stationary wings 302 that generate lift based on the wing shape and the vehicle's forward airspeed. This wing configuration is different from a rotorcraft's configuration, which produces lift through rotating rotors about a fixed mast, and an ornithopter's configuration, which produces lift by flapping wings.

FIG. 3A depicts some common structures used in a fixed-wing aircraft 300. In particular, fixed-wing aircraft 300 includes a fuselage 304, two horizontal wings 302 with an airfoil-shaped cross section to produce an aerodynamic force, a vertical stabilizer 306 (or fin) to stabilize the plane's yaw (turn left or right), a horizontal stabilizer 308 (also referred to as an elevator or tailplane) to stabilize pitch (tilt up or down), landing gear 310, and a propulsion unit 312, which can include a motor, shaft, and propeller.

Figure 3B:
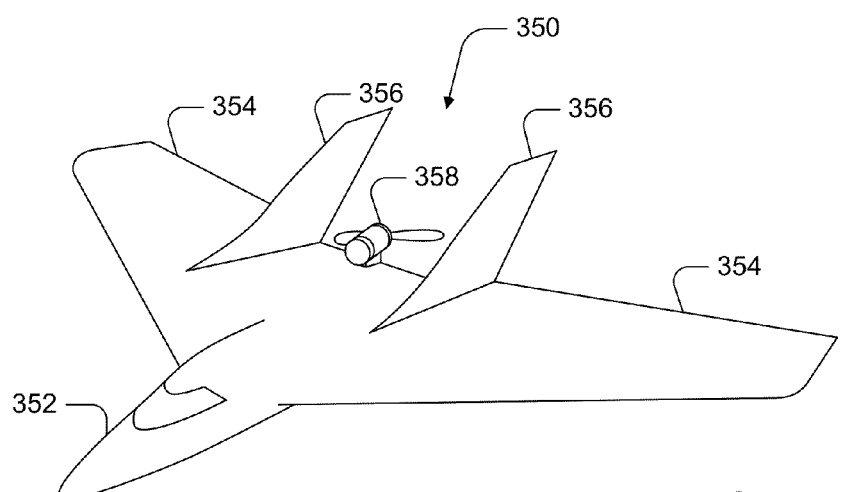

FIG. 3B shows an example of an aircraft 350 with a propeller in a pusher configuration. The term "pusher" refers to the fact that the propulsion unit 358 is mounted at the back of the aircraft and "pushes" the vehicle forward, in contrast to the propulsion unit being mounted at the front of the aircraft. Similar to the description provided for FIG. 3A, FIG. 3B depicts common structures used in the pusher plane: a fuselage 352, two horizontal wings 354, vertical stabilizers 356, and a propulsion unit 358, which can include a motor, shaft, and propeller.

UAVs can be launched in various ways, using various types of launch systems (which may also be referred to as deployment systems). A very simple way to launch a UAV is a hand launch. To perform a hand launch, a user holds a portion of the aircraft, preferably away from the spinning rotors, and throws the aircraft into the air while contemporaneously throttling the propulsion unit to generate lift.

Rather than using a hand launch procedure in which the person launching the vehicle is exposed to risk from the quickly spinning propellers, a stationary or mobile launch station can be utilized. For instance, a launch system can include supports, angled and inclined rails, and a backstop. The aircraft begins the launch system stationary on the angled and inclined rails and launches by sufficiently increasing the speed of the propeller to generate forward airspeed along the incline of the launch system. By the end of the angled and inclined rails, the aircraft can have sufficient airspeed to generate lift. As another example, a launch system may include a rail gun or cannon, either of which may launch a UAV by thrusting the UAV into flight. A launch system of this type may launch a UAV quickly and/or may launch a UAV far towards the UAV's destination. Other types of launch systems may also be utilized.

In some cases, there may be no separate launch system for a UAV, as a UAV may be configured to launch itself. For example, a "tail sitter" UAV typically has fixed wings to provide lift and allow the UAV to glide, but also is configured to take off and land vertically on its own. Other examples of self-launching UAVs are also possible.

In a further aspect, various other types of unmanned vehicles may be utilized to provide remote medical support. Such vehicles may include, for example, unmanned ground vehicles (UGVs), unmanned space vehicles (USVs), and/or unmanned underwater vehicles (UUVs). A UGV may be a vehicle which is capable of sensing its own environment and navigating surface-based terrain without input from a driver. Examples of UGVs include watercraft, cars, trucks, buggies, motorcycles, treaded vehicles, and retrieval duck decoys, among others. A UUV is a vehicle that is capable of sensing its own environment and navigating underwater on its own, such as a submersible vehicle. Other types of unmanned vehicles are possible as well.

III. ILLUSTRATIVE MEDICAL SUPPORT SYSTEMS WITH UAVS

As noted above, UAVs may be deployed to provide remote medical support. FIG. 4 is a simplified block diagram illustrating a medical support system 400, according to an example embodiment.

In an illustrative medical-support system 400, an access system 402 may allow for interaction with, control of, and/or utilization of a network of medical-support UAVs 404. In some embodiments, an access system 402 may be a computing system that allows for human-controlled dispatch of UAVs 404. As such, the control system may include or otherwise provide a user interface (UI) 403 via which a user can access and/or control UAVs 404.

As a specific example, access system 402 could be a computing system at a police station or a fire station. Accordingly, a human operator at the police or fire station may receive an indication that a situation exists from a remote device 406 (e.g., a phone call, text message, etc.). The operator may then determine that medical support is appropriate and utilize access system 402 to dispatch one or more UAVs to provide the appropriate medical support. For example, the operator may use the UI 403 of access system 402 to request that a UAV be dispatched to the location of remote device 406 (or to another location indicated by the user of the remote device 406).

A UI 403 of an access system 402 may provide other functionality in addition to allowing for dispatch of UAVs 404. For example, UI 403 may allow an operator to specify certain details related to the medical situation to which the UAV is being dispatched. Examples of such details may include, but are not limited to: (a) general information related to the person or persons involved in the situation, such as age, height, weight, and so on, (b) medical information related to the person or persons involved in the situation, such as medical history, known allergies, and so on, (c) information related to the medical situation itself, such as symptoms exhibited by a person, details of events surrounding the situation (e.g., a car accident), and so on, and (d) desired specifications for the UAV to be dispatched, such as medical-support capabilities, wireless-communication capabilities, and so on.

Further, an access system 402 may provide for remote operation of a UAV. For instance, an access system 402 may allow an operator to control the flight of a UAV via UI 403. As a specific example, an operator may use an access system to dispatch a UAV 404 to the scene of a medical situation. The UAV 404 may then autonomously navigate to the general area where the medical situation is believed to exist (e.g., a stadium). At this point, the operator may use the access system 402 to take over control of the UAV 404, and navigate the UAV to the particular person in need of medical support (e.g., to the person's seat within the stadium). Other examples are also possible.

In an illustrative embodiment, UAVs 404 may take various forms. For example, each UAV 404 may be a UAV such as those illustrated in FIGS. 1, 2, 3A, and 3B. However, medical support system 400 may also utilize other types of UAVs without departing from the scope of the invention. In some implementations, all UAVs 404 may be of the same or a similar configuration. However, in other implementations, UAVs 404 may include a number of different types of UAVs. For instance, UAVs 404 may include a number of types of UAVs, with each type of UAV being configured for a different type or types of medical support.

A remote device 406 may take various forms. Generally, a remote device 406 may be any device via which a request for medical support can be made and/or via which a situation that may require or benefit from medical support can be reported. For instance, a remote device 406 may be a mobile phone, tablet computer, laptop computer, personal computer, or any network-connected computing device. Further, in some instances, remote device 406 may not be a computing device. As an example, a standard telephone, which allows for communication via plain old telephone service (POTS), may serve as a remote device 406.

Further, a remote device 406 may be configured to communicate with access system 402 via one or more types of communication network(s) 414. For example, a remote device 406 could communicate with access system 402 (or via a human operator of the access system) by placing a phone call over a POTS network, a cellular network, and/or a data network such as the Internet. Other types of networks may also be utilized.

As noted above, a remote device 406 may be configured to allow a user to request medical support. For example, a person may use their mobile phone, a POTS phone, or a VoIP phone, to place an emergency call (e.g., a 9-1-1 call) and request that medical support be provided at the scene of an accident. Further, note that a request for medical support need not be explicit. For instance, a person may place a 9-1-1 call to report an emergency situation. When the 9-1-1 operator receives such a call, the operator may evaluate the information that is provided and decide that medical support is appropriate. Accordingly, the operator may use an access system 402 to dispatch a UAV 404.

In a further aspect, a remote device 406 may be configured to determine and/or provide an indication of its own location. For example, remote device 406 may include a GPS system so that it can include GPS location information (e.g., GPS coordinates) in a communication to an access system 402 and/or to a dispatch system such as central dispatch system 408. As another example, a remote device 406 may use a technique that involves triangulation (e.g., between base stations in a cellular network) to determine its location. Alternatively, another system such as a cellular network may use a technique that involves triangulation to determine the location of a remote device 406, and then send a location message to the remote device 406 to inform the remote device of its location. Other location-determination techniques are also possible.

In an illustrative arrangement, central dispatch system 408 may be a server or group of servers, which is configured to receive dispatch messages requests and/or dispatch instructions from an access system 402. Such dispatch messages may request or instruct the central dispatch system 408 to coordinate the deployment of UAVs for remote medical support. A central dispatch system 408 may be further configured to route such requests or instructions to local dispatch systems 410. To provide such functionality, central dispatch system 408 may communicate with access system 402 via a data network, such as the Internet or a private network that is established for communications between access systems and automated dispatch systems.

In the illustrated configuration, central dispatch system 408 may be configured to coordinate the dispatch of UAVs 404 from a number of different local dispatch systems 410. As such, central dispatch system 408 may keep track of which UAVs 404 are located at which local dispatch systems 410, which UAVs 404 are currently available for deployment, and/or which medical situation or situations each of the UAVs 404 is configured for. Additionally or alternatively, each local dispatch system 410 may be configured to track which of its associated UAVs 404 are currently available for deployment and/or which medical situation or situations each of its associated UAVs is configured for.

In some embodiments, when central dispatch system 408 receives a request for medical support from an access system 402, central dispatch system 408 may select a specific UAV 404 to dispatch. The central dispatch system 408 may accordingly instruct the local dispatch system 410 that is associated with the selected UAV to dispatch the selected UAV. The local dispatch system 410 may then operate its associated deployment system 412 to launch the selected UAV.

As a specific example, central dispatch system 408 may receive a request for medical support that indicates a certain type of medical situation and a location where the situation is occurring. Take, for instance, a request for medical support at the home of a person who appears to have suffered from cardiac arrest. In this scenario, the central dispatch system 408 may evaluate the fleet of UAVs 404 to select the closest available UAV to the person's home that is configured to provide medical support when a heart attack has occurred. Alternatively, the central dispatch system 408 may select an available UAV that is within a certain distance from the person's home (which may or may not be the closest), and which is configured to provide medical support when cardiac arrest has occurred.

In other embodiments, a central dispatch system 408 may forward a request for medical support to a local dispatch system 410 that is near the location where the support is requested, and leave the selection of a particular UAV 404 to the local dispatch system 410. For instance, in a variation on the above example, central dispatch system 408 may forward a request for medical support at the home of a person who appears to have suffered from a heart attack to the local dispatch system 410 that is closest to, or within a certain distance from, the person's home. Upon receipt of the request, the local dispatch system 410 may then determine which of its associated UAVs is configured to provide medical support to a heart-attack victim, and deploy this UAV.

In an example configuration, a local dispatch system 410 may be implemented in a computing system at the same location as the deployment system or systems 412 that it controls. For example, in some embodiments, a local dispatch system 410 could be implemented by a computing system at a building, such as a fire station, where the deployment systems 412 and UAVs 404 that are associated with the particular local dispatch system 410 are also located. In other embodiments, a local dispatch system 410 could be implemented at a location that is remote to its associated deployment systems 412 and UAVs 404.

Numerous variations on and alternatives to the illustrated configuration of medical support system 400 are possible. For example, in some embodiments, a user of a remote device 406 could request medical support directly from a central dispatch system 408. To do so, an application may be implemented on a remote device 406 that allows the user to provide information regarding a medical situation, and generate and send a data message to request medical support. Such an application might also allow the user to request a particular type of medical support (e.g., by requesting that a UAV deliver a certain kind of medicine). In such an embodiment, central dispatch system 408 may include automated functionality to handle requests that are generated by such an application, evaluate such requests, and, if appropriate, coordinate with an appropriate local dispatch system 410 to deploy a UAV.

Further, in some implementations, some or all of the functionality that is attributed herein to central dispatch system 408, local dispatch system(s) 410, access system 402, and/or deployment system(s) 412 could be combined in a single system, implemented in a more complex system, and/or redistributed among central dispatch system 408, local dispatch system(s) 410, access system 402, and/or deployment system(s) 412 in various ways.

Yet further, while each local dispatch system 410 is shown as having two associated deployment systems, a given local dispatch system 410 may have more or less associated deployment systems. Similarly, while central dispatch system 408 is shown as being in communication with two local dispatch systems 410, a central dispatch system may be in communication with more or less local dispatch systems 410.

In a further aspect, a deployment system 412 may take various forms. In general, a deployment system may take the form of or include a system for physically launching a UAV 404. Further, a deployment system 412 may be configured to launch one particular UAV 404, or to launch multiple UAVs 404. A deployment system 412 may further be configured to provide additional functions, including for example, diagnostic-related functions such as verifying system functionality of the UAV, verifying functionality of devices that are housed within a UAV (e.g., such as a defibrillator, a mobile phone, or an HMD), and/or maintaining devices or other items that are housed in the UAV (e.g., by charging a defibrillator, mobile phone, or HMD, or by checking that medicine has not expired).

In some embodiments, the deployment systems 412 and their corresponding UAVs 404 (and possibly associated local dispatch systems 410) may be strategically distributed throughout an area such as a city. For example, deployment systems 412 may be located on the roofs of certain municipal buildings, such as fire stations, which can thus serve as the dispatch locations for UAVs 404. Fire stations may function well for UAV dispatch, as fire stations tend to be distributed well with respect to population density, their roofs tend to be flat, and the use of firehouse roofs as leased spaces for UAV dispatch could further the public good. However, deployment systems 412 (and possibly the local dispatch systems 410) may be distributed in other ways, depending upon the particular implementation.

In a further aspect, a medical-support system 400 may include or have access to a user-account database 414. The user-account database 414 may include data for a number of user-accounts, which are each associated with one or more person. For a given user-account, the user-account database 414 may include data related to the associated person or persons' medical history and/or may include other data related to the associated person or persons. Note that the medical-support system may only acquire, store, and utilize data related to a person with that person's explicit permission to do so.

Further, in some embodiments, a person may have to register for a user-account with the medical-support system 400 in order to use or be provided with medical support by the UAVs 404 of medical-support system 400. As such, the user-account database 414 may include authorization information for a given user-account (e.g., a user-name and password), and/or other information that may be used to authorize access to a user-account.

In some embodiments, a person may associate one or more of their devices with their user-account, such that they can be provided with access to the services of medical-support system 400. For example, when a person uses an associated mobile phone to, e.g., place a call to an operator of access system 402 or send a message requesting medical support to a dispatch system, the phone may be identified via a unique device identification number, and the call or message may then be attributed to the associated user-account. In addition or in the alternative to being an authorization mechanism, identifying the user-account may allow information such as the person's medical history to be used in responding to their request for medical support.

In a further aspect, the user-account database 414 may include data indicating a service level for each user. More specifically, a medical-support system 400 may provide service according to a number of different service levels, which correspond to different types of medical support. For example, a higher service level may: (a) provide access to additional types of UAVs, (b) provide medical support for additional medical situations, (c) provide access to improved support for a given medical situation, and/or (d) have priority as far as response time to requests for medical support, as compared to a lower service level. Other differences between a higher and lower service level are also possible.

In some embodiments, there may be no individual user accounts associated with a medical system; or, user accounts may exist but may not be used for purposes of determining whether a person should be provided medical support and/or for purposes of determining the quality of medical support that should be provided. For example, a medical support system may be implemented by a municipality or another public entity to provide medical support to citizens for free or at an equal cost. Other examples are also possible.

IV. ILLUSTRATIVE COMPONENTS OF A MEDICAL-SUPPORT UAV

Figure 5:
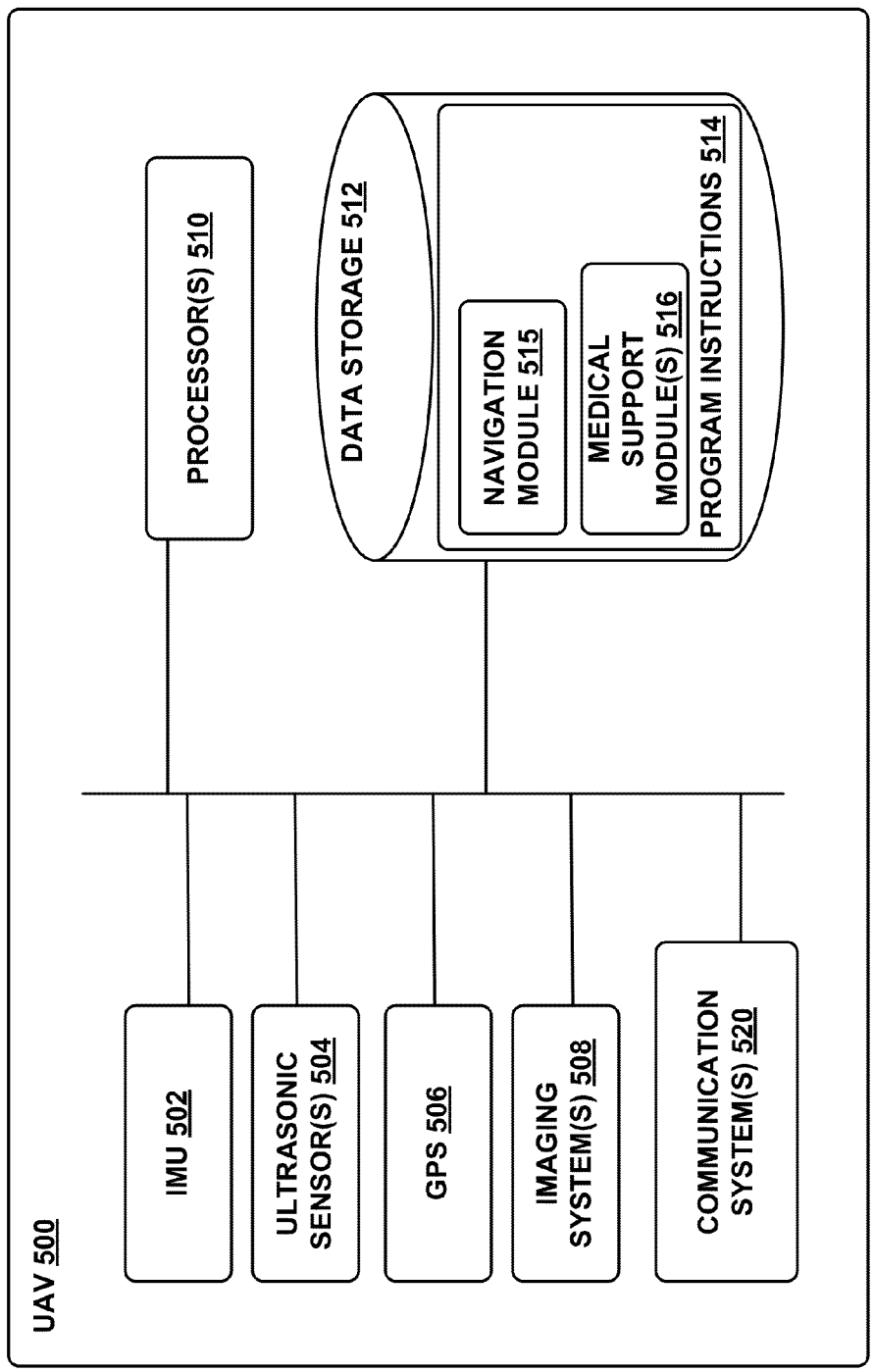
FIG. 5 is a simplified block diagram illustrating components of an unmanned aerial vehicle, according to an example embodiment.

FIG. 5 is a simplified block diagram illustrating components of a UAV 500, according to an example embodiment. UAV 500 may take the form of or be similar in form to one of the UAVs 100, 200, 300, and 350 shown in FIGS. 1, 2, 3A, and 3B. However, a UAV 500 may also take other forms.

UAV 500 may include various types of sensors, and may include a computing system configured to provide the functionality described herein. In the illustrated embodiment, the sensors of UAV 500 include an inertial measurement unit (IMU) 502, ultrasonic sensor(s) 504, GPS 506, imaging system(s) 508, among other possible sensors and sensing systems.

In the illustrated embodiment, UAV 500 also includes one or more processors 510. A processor 510 may be a general-purpose processor or a special purpose processor (e.g., digital signal processors, application specific integrated circuits, etc.). The one or more processors 510 can be configured to execute computer-readable program instructions 514 that are stored in the data storage 512 and are executable to provide the functionality of a UAV described herein.

The data storage 512 may include or take the form of one or more computer-readable storage media that can be read or accessed by at least one processor 510. The one or more computer-readable storage media can include volatile and/or non-volatile storage components, such as optical, magnetic, organic or other memory or disc storage, which can be integrated in whole or in part with at least one of the one or more processors 510. In some embodiments, the data storage 512 can be implemented using a single physical device (e.g., one optical, magnetic, organic or other memory or disc storage unit), while in other embodiments, the data storage 512 can be implemented using two or more physical devices.

As noted, the data storage 512 can include computer-readable program instructions 514 and perhaps additional data, such as diagnostic data of the UAV 500. As such, the data storage 514 may include program instructions to perform or facilitate some or all of the UAV functionality described herein. For instance, in the illustrated embodiment, program instructions 514 include a navigation module 515 and one or more medical-support modules 516.

A. Sensors

In an illustrative embodiment, IMU 502 may include both an accelerometer and a gyroscope, which may be used together to determine the orientation of the UAV 500. In particular, the accelerometer can measure the orientation of the vehicle with respect to earth, while the gyroscope measures the rate of rotation around an axis. IMUs are commercially available in low-cost, low-power packages. For instance, an IMU 502 may take the form of or include a miniaturized MicroElectroMechanical System (MEMS) or a NanoElectroMechanical System (NEMS). Other types of IMUs may also be utilized.

An IMU 502 may include other sensors, in addition to accelerometers and gyroscopes, which may help to better determine position and/or help to increase autonomy of the UAV 500. Two examples of such sensors are magnetometers and pressure sensors. Other examples are also possible. (Note that a UAV could also include such additional sensors as separate components from an IMU.)

While an accelerometer and gyroscope may be effective at determining the orientation of the UAV 500, slight errors in measurement may compound over time and result in a more significant error. However, an example UAV 500 may be able mitigate or reduce such errors by using a magnetometer to measure direction. One example of a magnetometer is a low-power, digital 3-axis magnetometer, which can be used to realize an orientation independent electronic compass for accurate heading information. However, other types of magnetometers may be utilized as well.

UAV 500 may also include a pressure sensor or barometer, which can be used to determine the altitude of the UAV 500. Alternatively, other sensors, such as sonic altimeters or radar altimeters, can be used to provide an indication of altitude, which may help to improve the accuracy of and/or prevent drift of an IMU.

In a further aspect, UAV 500 may include one or more sensors that allow the UAV to sense objects in the environment. For instance, in the illustrated embodiment, UAV 500 includes ultrasonic sensor(s) 504. Ultrasonic sensor(s) 504 can determine the distance to an object by generating sound waves and determining the time interval between transmission of the wave and receiving the corresponding echo off an object. A typical application of an ultrasonic sensor for unmanned vehicles or IMUs is low-level altitude control and obstacle avoidance. An ultrasonic sensor can also be used for vehicles that need to hover at a certain height or need to be capable of detecting obstacles. Other systems can be used to determine, sense the presence of, and/or determine the distance to nearby objects, such as a light detection and ranging (LIDAR) system, laser detection and ranging (LADAR) system, and/or an infrared or forward-looking infrared (FLIR) system, among other possibilities.

UAV 500 also includes a GPS receiver 506. The GPS receiver 506 may be configured to provide data that is typical of well-known GPS systems, such as the GPS coordinates of the UAV 500. Such GPS data may be utilized by the UAV 500 for various functions. For example, when a caller uses a mobile device to request medical support from a UAV, the mobile device may provide its GPS coordinates. As such, the UAV may use its GPS receiver 506 to help navigate to the caller's location, as indicated, at least in part, by the GPS coordinates provided by their mobile device. Other examples are also possible.

UAV 500 may also include one or more imaging system(s) 508. For example, one or more still and/or video cameras may be utilized by a UAV 500 to capture image data from the UAV's environment. As a specific example, charge-coupled device (CCD) cameras or complementary metal-oxide-semiconductor (CMOS) cameras can be used with unmanned vehicles. Such imaging sensor(s) 508 have numerous possible applications, such as obstacle avoidance, localization techniques, ground tracking for more accurate navigation (e,g., by applying optical flow techniques to images), video feedback, and/or image recognition and processing, among other possibilities.

In a further aspect, UAV 500 may use its one or more imaging system 508 to help in determining location. For example, UAV 500 may capture imagery of its environment and compare it to what it expects to see in its environment given current estimated position (e.g., its current GPS coordinates), and refine its estimate of its position based on this comparison.

In a further aspect, UAV 500 may include one or more microphones. Such microphones may be configured to capture sound from the UAVs environment.

B. Navigation and Location Determination

The navigation module 515 may provide functionality that allows the UAV 500 to, e.g., move about in its environment and reach a desired location. To do so, the navigation module 515 may control the altitude and/or direction of flight by controlling the mechanical features of the UAV that affect flight (e.g., rotors 110 of UAV 100).

In order to navigate the UAV 500 to a target location, a navigation module 515 may implement various navigation techniques, such as map-based navigation and localization-based navigation, for instance. With map-based navigation, the UAV 500 may be provided with a map of its environment, which may then be used to navigate to a particular location on the map. With localization-based navigation, the UAV 500 may be capable of navigating in an unknown environment using localization. Localization-based navigation may involve a UAV 500 building its own map of its environment and calculating its position within the map and/or the position of objects in the environment. For example, as a UAV 500 moves throughout its environment, the UAV 500 may continuously use localization to update its map of the environment. This continuous mapping process may be referred to as simultaneous localization and mapping (SLAM). Other navigation techniques may also be utilized.

In some embodiments, the navigation module 515 may navigate using a technique that relies on waypoints. In particular, waypoints are sets of coordinates that identify points in physical space. For instance, an air-navigation waypoint may be defined by a certain latitude, longitude, and altitude. Accordingly, navigation module 515 may cause UAV 500 to move from waypoint to waypoint, in order to ultimately travel to a final destination (e.g., a final waypoint in a sequence of waypoints).

In a further aspect, navigation module 515 and/or other components and systems of UAV 500 may be configured for "localization" to more precisely navigate to the scene of a medical situation. More specifically, it may be desirable in certain situations for a UAV to be close to the person in need of medical support (e.g., within reach of the person), so as to properly provide medical support to the person. To this end, a UAV may use a two-tiered approach in which it uses a more-general location-determination technique to navigate to a target location or area that is associated with the medical situation, and then use a more-refined location-determination technique to identify and/or navigate to the target location within the general area.

For example, a UAV 500 may navigate to the general area of a person in need using waypoints that are pre-determined based on GPS coordinates provided by a remote device at the scene of the medical situation. The UAV may then switch to mode in which it utilizes a localization process to locate and travel to a specific location of the person in need. For example, if a person is having a heart attack at a large stadium, a UAV 500 carrying a medical package may need to be within reach of the person or someone near the person so that the can take items from the package. However, a GPS signal may only get a UAV so far, e.g., to the stadium. A more precise location-determination technique may then be used to find the specific location of the person within the stadium.

Various types of location-determination techniques may be used to accomplish localization of a person once a UAV 500 has navigated to the general area of the person. For instance, a UAV 500 may be equipped with one or more sensory systems, such as, for example, imaging system(s) 508, a directional microphone array (not shown), ultrasonic sensors 504, infrared sensors (not shown), and/or other sensors, which may provide input that the navigation module 515 utilizes to navigate autonomously or semi-autonomously to the specific location of a person.

As another example, once the UAV 500 reaches the general area of the person, the UAV 500 may switch to a "fly-by-wire" mode where it is controlled, at least in part, by a remote operator, who can navigate the UAV 500 to the specific location of the person in need. To this end, sensory data from the UAV 500 may be sent to the remote operator to assist them in navigating the UAV to the specific location. For example, the UAV 500 may stream a video feed or a sequence of still images from the UAV's imaging system(s) 508. Other examples are possible.

As yet another example, the UAV 500 may include a module that is able to signal to a passer-by for assistance in either reaching the specific location or delivering its medical-support items to the medical situation; for example, by displaying a visual message in a graphic display, playing an audio message or tone through speakers, flashing a light, or performing a combination of such functions. Such visual or audio message might indicate that assistance is needed in delivering the UAV 500 to the person in need, and might provide information to assist the passer-by in delivering the UAV 500 to the person, such a description of the person, the person's name, and/or a description of the person's specific location, among other possibilities. This implementation can be useful in a scenario in which the UAV is unable to use sensory functions or another location-determination technique to determine the specific location of the person.

As an additional example, once a UAV 500 arrives at the general area of a person, the UAV may utilize a beacon from the remote device (e.g., the mobile phone of a person who called for medical support) to locate the person. Such a beacon may take various forms. As an example, consider the scenario where a remote device, such as the mobile phone of a person in need or a bystander, is able to send out directional signals (e.g., an RF signal, a light signal and/or an audio signal). In this scenario, the UAV may be configured to navigate by "sourcing" such directional signals—in other words, by determining where the signal is strongest and navigating accordingly. As another example, a mobile device can emit a frequency, either in the human range or outside the human range, and the UAV can listen for that frequency and navigate accordingly. As a related example, if the UAV is listening for spoken commands, then the UAV could utilize spoken statements, such as "Help! I'm over here!" to source the specific location of the person in need of medical assistance.

In an alternative arrangement, a navigation module may be implemented at a remote computing device, which communicates wirelessly with the UAV. The remote computing device may receive data indicating the operational state of the UAV, sensor data from the UAV that allows it to assess the environmental conditions being experienced by the UAV, and/or location information for the UAV. Provided with such information, the remote computing device may determine altitudinal and/or directional adjustments that should be made by the UAV and/or may determine how the UAV should adjust its mechanical features (e.g., rotors 110 of UAV 100) in order to effectuate such movements. The remote computing system may then communicate such adjustments to the UAV so it can move in the determined manner.

C. Communication Systems

In a further aspect, UAV 500 includes one or more communication systems 520. The communications systems 520 may include one or more wireless interfaces and/or one or more wireline interfaces, which allow UAV 500 to communicate via one or more networks. Such wireless interfaces may provide for communication under one or more wireless communication protocols, such as Bluetooth, WiFi (e.g., an IEEE 802.11 protocol), Long-Term Evolution (LTE), WiMAX (e.g., an IEEE 802.16 standard), a radio-frequency ID (RFID) protocol, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network.

In an example embodiment, a UAV 500 may include communication systems 520 that allow for both short-range communication and long-range communication. For example, the UAV 500 may be configured for short-range communications using Bluetooth and for long-range communications under a CDMA protocol. In such an embodiment, the UAV 500 may be configured to function as a "hot spot;" or in other words, as a gateway or proxy between a remote support device and one or more data networks, such as cellular network and/or the Internet. Configured as such, the UAV 500 may facilitate data communications that the remote support device would otherwise be unable to perform by itself.

For example, UAV 500 may provide a WiFi connection to a remote device, and serve as a proxy or gateway to a cellular service provider's data network, which the UAV might connect to under an LTE or a 3G protocol, for instance. The UAV 500 could also serve as a proxy or gateway to a high-altitude balloon network, a satellite network, or a combination of these networks, among others, which a remote device might not be able to otherwise access.

D. Power Systems

In a further aspect, UAV 500 may include power system(s) 521. A power system 521 may include one or more batteries for providing power to the UAV 500. In one example, the one or more batteries may be rechargeable and each battery may be recharged via a wired connection between the battery and a power supply and/or via a wireless charging system, such as an inductive charging system that applies an external time-varying magnetic field to an internal battery.

E. Medical-Support Functionality

As noted above, UAV 500 may include one or more medical-support modules 516. The one or more medical-support modules 516 include software, firmware, and/or hardware that may help to provide or assist in the provision of the medical-support functionality described herein.

Configured as such, a UAV 500 may provide medical support in various ways. For instance, a UAV 500 may have stored information that can be provided to a person or persons at the target location, in order to assist the person or persons in providing medical care. For example, a UAV may include a video or audio file with instructions for providing medical support, which the UAV can play out to a person at the target location. As another example, a UAV may include an interactive program to assist a person at the target location in providing medical support. For instance, a UAV may include an application that analyzes the person's speech to detect questions related to the medical situation and/or that provides a text-based interface via which the person can ask such questions, and then determines and provides answers to such questions.

In some embodiments, a UAV 500 may facilitate communication between a layperson and/or medical personnel at the scene and medical personnel at a remote location. As an example, a medical support module 516 may provide a user interface via which a person at the scene can use a communication system 520 of the UAV to communicate with an emergency medical technician at a remote location. As another example, the UAV 500 can unlock certain capabilities of a remote device, such as a mobile phone, which is near the UAV at the scene of a medical situation. Such capabilities may be inaccessible to a user of the remote device, unless the remote device is within a certain distance from the UAV such that the UAV can unlock the capabilities. For example, a UAV may send the remote device a security key that allows the remote device to establish a secure connection to communicate with medical personnel at a remote location. Other examples are also possible.

Further, in order to provide medical support at a remote location, a UAV 500 may be configured to transport items to the scene of a medical situation. Such items may aid in diagnosing and/or treating a person who needs medical assistance, or may serve other purposes. Such items may include, as examples: (a) medicines, (b) diagnostic devices, such as a pulse oximeter, blood pressure sensor, or EKG sensor, (c) treatment devices, such as an EpiPen, a first aid kit, or various kinds of defibrillators (e.g., an automated external defibrillator (AED)), and/or (d) remote support devices, such as a mobile phone or a head-mountable device (HMD), among other possibilities. Note that some items that are electronic may include one or more batteries to provide power to the item. These batteries may be rechargeable and may be recharged using one or more wired or wireless charging systems. In addition or on in the alternative, an item may be integrated with one or more batteries in the power system 521 for power.

A UAV 500 may employ various systems and configurations in order to transport items to the scene of a medical situation. For example, as shown in FIG. 1, a UAV 100 can include a compartment 135, in which an item or items may be transported. As another example, the UAV can include a pick-and-place mechanism, which can pick up and hold the item while the UAV is in flight, and then release the item during or after the UAV's descent. As yet another example, a UAV could include an air-bag drop system, a parachute drop system, and/or a winch system that is operable from high above a medical situation to drop or lower an item or items to the scene of the medical situation. Other examples are also possible.

In some implementations, a given UAV 500 may include a "package" designed for a particular medical situation (or possibly for a particular set of medical situations). A package may include one or more items for medical support in the particular medical situation, and/or one or more medical-support modules 516 that are designed to provide medical support in the particular medical situation. In some cases, a UAV 500 may include a package that is designed for a particular medical situation such as choking, cardiac arrest, shock, asthma, drowning, etc.

In other cases, a UAV 500 may include a package that is designed for a number of different medical situations, which may be associated in some way. For example, a dive-accident package may be designed to provide or assist in provision of care in various medical situations that are often associated with a scuba diving accident, such as drowning and/or decompression sickness. Such a dive-accident package might include a flotation device, an oxygen-therapy system, a system for delivering visual and/or audible medical care instructions (e.g., instructions for performing CPR), and/or a signaling device, among other possibilities. A UAV 500 that is configured with such a dive-accident package may be referred to herein as a "dive-rescue" UAV. Such a dive-rescue UAV may be deployed to a diver on the surface of the water, who has just had an accident while scuba diving, with the hope that the UAV can reach the diver and deliver medical treatment sooner than would otherwise be possible.

For instance, provided with the above dive-accident package, the UAV 500 may drop a flotation device to help the diver stay afloat until the diver can be reached by rescuers. In addition, the UAV may include a signaling device, which can be automatically turned on when the UAV locates the diver. Doing so may help a rescue boat locate a diver more quickly. Further, once the diver has been rescued, the UAV may display visual instructions and/or play back auditory instructions for CPR, which may help to revive a drowning victim. Such instructions may be particularly useful in the case where the diver is rescued by non-medical professionals; if the diver is rescued by a passing fishing boat, for example.

Further, when the UAV arrives at the scene of a dive accident or, more likely, once the diver has been moved to a rescue boat, the UAV could provide an oxygen-therapy system, and possibly instructions for use thereof, in order to treat possible decompression sickness. Since a rescue boat might not have oxygen-therapy system, and immediate administration of pure oxygen has been shown to increase the probability of recovering from decompression sickness, such functionality of a UAV could improve treatment for a diver suffering from decompression sickness.

In some embodiments, a UAV 500 could include an integrated system or device for administering or assisting in the administration of medical care (e.g., a system or device having one or more components that are built in to the structure of the UAV itself). For example, as noted above, a UAV could include an oxygen-therapy system. In an example configuration, an oxygen-therapy system might include a mask that is connected via tubing to an on-board oxygen source. Configured as such, the UAV could release the oxygen mask when it reaches a person in need of oxygen (e.g., at a fire scene).

As another example of a UAV with an integrated medical-support device, a UAV 500 might function as a mobile defibrillator. Specifically, rather than carry a stand-alone defibrillator that can then be removed from the UAV for use, the UAV itself may function as a defibrillator.

As a specific example, a multicopter might include components of an AED that is built into its body, as well as retractable electrode pads for administering a shock to a person who is experiencing a cardiac event or arrest. When the multicopter arrives at the scene of cardiac arrest, the multicopter may land, disable its rotors, and enter a mode where it functions as an AED. Specifically, after landing, the multicopter may release its retractable electrode pads and provide instructions so that a bystander, who might be layperson, could use the electrode pads to administer care to the person with a cardiac arrest. Such instructions may be provided, for example, by displaying text and/or video on a graphic display that is built in to the body of the multicopter, and/or by playing back audio instructions. The multicopter could also include a wireless communication interface via which a bystander could communicate with a live remote operator (e.g., a medical professional at a remote location), in order to receive instructions for using the AED.

Many other examples and variations on the above examples of UAVs with integrated medical-support systems and devices are also possible. For instance, a medical device may be integrated into the structure of a UAV itself when doing so reduces weight, improves aerodynamics, and/or simplifies the use of the device by a person at the scene of the medical situation. Further, those skilled in the art will appreciate that a medical-support system or device may be integrated in the structure of a UAV in other situations and for other reasons.

In some applications, a UAV 500 may be dispatched to the scene of a medical situation to provide early intelligence to medical personnel. In particular, a UAV 500 may be dispatched because it is expected to reach the location of a medical situation more rapidly than medical personnel are able to. In this scenario, the UAV 500 may arrive at the scene and provide early intelligence by communicating information and providing situational awareness to medical personnel. For example, a UAV 500 may use its imaging system(s) 508 to capture video and/or still images at the scene of the medical situation, which the UAV 500 may communicate to medical and/or emergency personnel. As another example, UAV 500 could administer preliminary tests to a person in need, or request that a bystander administer certain preliminary diagnostic tests and/or provide certain information. UAV 500 may then send such test results and/or such information provided by a bystander to medical and/or emergency personnel. A UAV 500 may provide other types of early-intelligence information as well.

By providing early intelligence to medical and/or emergency personnel, a UAV 500 may help the medical and/or emergency personnel to prepare to provide care, such that more effective care can be provided once the personnel arrive at the scene. For instance, a UAV 500 could send video, test results, and/or bystander-provided information to medical personnel while they are travelling in an ambulance on their way to the scene, to firemen or other personnel while they are in a fire truck on their way to the scene, and/or to police they are in a law-enforcement vehicle on their way to the scene, among other possibilities.

It should be understood that the examples of medical-support functionality that are provided herein are not intended to be limited. A UAV may be configured to provide other types of medical-support functionality without departing from the scope of the invention.

V. ILLUSTRATIVE METHODS

Figure 6:
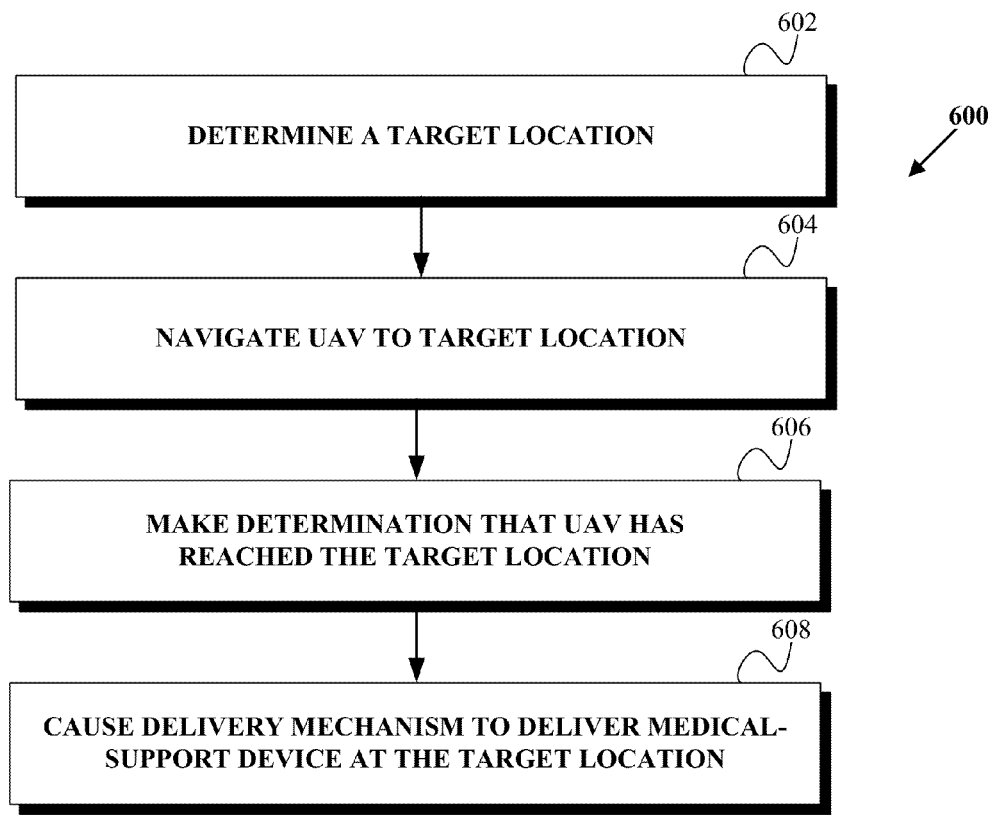
FIG. 6 is a flow chart illustrating method 600, according to an example embodiment.

FIG. 6 is a flow chart illustrating a method 600, according to an example embodiment. Method 600 may be implemented by a UAV in order to provide a medical-support device to a target location associated with a medical situation using a housing that is configured to hold the medical-support device, and then using a control system that is configured to deliver the medical support device to the target location.

Illustrative methods, such as method 600, may be implemented by a UAV, such as the UAVs described in reference to FIGS. 1 to 3, or by one or more components of such UAVs. For instance, an example method may be carried out by a medical-support module, a navigation module, and/or a control system of a UAV, or by a combined system, among other possibilities. In other embodiments, some or all of an example method may be carried out by a remote computing device that is in communication with a UAV. For example, some or all of an exemplary method may be carried out by the medical-support system, such as by one or more of the components of the medical-support system shown in FIG. 4.

Referring to FIG. 6 in more detail, method 600 involves a UAV determining a target location associated with a medical situation, as shown in block 602. The UAV may then navigate to the target location through the use of a navigation system and/or control system, among other possibilities, as shown in block 604. Further, the UAV may make a determination that the UAV has reached the target location, as shown in block 606. In response to the determination, the UAV may deliver a medical-support device to the target location, as shown by block 608.

A. Determining the Target Location

As noted above, block 602 of method 600 involves a UAV determining a target location that is associated with a medical situation. Various techniques may be used to determine the target method.

Further, the target location may take various forms. For example, the target location could be provided in the form of GPS coordinates, a certain latitude and longitude, a street address, and/or a certain place (e.g., a particular building, stadium, landmark, or park), among other possibilities.

In some embodiments, the target location may be an estimated location of the person or persons who are likely to benefit from medical support in the given medical situation. For example, if a person who is in need of medical care places an emergency call from their own mobile phone, the target location may be determined to be or otherwise based on the location of their mobile phone. As another example, if a bystander places an emergency call from their mobile phone in order to report a medical situation that involves another person, it may be assumed or otherwise determined that the bystander is at or near the location of the other person. Accordingly, the target location may be set to (or otherwise determined from) the location of the bystander's mobile phone.

In other embodiments, the target location may be different from the location of the person or persons who are likely to benefit from medical support. For example, consider a scenario where an emergency medical technician (EMT) or paramedic is closer to the location of a person in need of medical support, but the EMT or paramedic does not have certain medical supplies that are needed for or might improve the medical care that can be provided. In this scenario, a medical support system (MSS) may dispatch a UAV to the location of the EMT or paramedic in order to deliver medical supplies to the EMT or paramedic, so that they can take them with them to the scene of the medical situation. Further, in some cases, the UAV might even be configured to deliver the medical supplies to the EMT or paramedic as they travel to the scene of the medical situation. In such case, the target location (e.g., the location of the EMT or paramedic) may be dynamically updated to reflect the movement of the EMT or paramedic as they travel to the scene.

In some embodiments, the target location may in fact be a location from a set of possible locations. For example, the target location may be any location within a certain distance from a particular location. As a specific example, the target location may be any location within 100 feet from the GPS coordinates provided by the remote device from which medical support was requested. As such, the target location may in fact be a target area (e.g., an area within a 100-foot radius from the location of the remote device). In another example, the target location may be any location within 500 feet north and/or south of the location of the remote device. Additional distances and shapes may be possible depending on the particular implementation or application of the remote device.

Note that in an example embodiment, method 600 may be carried out entirely by a UAV. As such, the determination of the target location at block 602 may simply involve the UAV receiving a data message that indicates the target location, such as a message indicating the GPS coordinates of a remote device from which medical support was requested, for instance. As such, the logic to actively determine what the target location is for a given medical situation may be implemented at a component or component of a MSS, such as an access system and/or a dispatch system.

In a further aspect, the target location may be determined based on a various types of location information. For instance, in some embodiments, the target location may be determined based on location information that is provided by the remote device from which the indication of the medical situation was received. For example, consider a scenario where a bystander calls "911" and says "Somebody near me just collapsed!" Typically, when receiving a phone call, the police also receive location information, such as GPS coordinates, which identify the location of the remote device. This location information may then be made available to a MSS or otherwise accessible for purposes of determining the target location (e.g., via an E911 system). For example, when a remote device calls to report a medical situation, an operator at an access system or an automated dispatch system could determine the location of the remote device based on such received GPS coordinates.

A MSS may determine and/or be provided with information that the can be used to determine the target location in other ways. For instance, in some embodiments, part or all of the process of determining the target location could be automated or, in other words, performed without a need for human intervention. To this end, the MSS could utilize any suitable information-recognition technique, such as, for example, voice recognition (when the notification is spoken) or character recognition (when the notification is typed), among other techniques now known or later developed. As an example, consider a scenario where a bystander calls "911" and says: "Somebody near me just collapsed! I'm at 123 Main Street, Mountain View." In this situation, an automated dispatch system could apply speech-to-text processing to analyze the bystander's words and determine the stated address therefrom.

Other types of location information may also be utilized to determine the target location. For example, the MSS may obtain location information from image data that is captured by a remote device at the scene of a medical situation, and sent from the remote device to a MSS. For example, a notifier may use the camera of their mobile phone to capture and send video and/or still images to the MSS, possibly in real-time. A component of a MSS could then analyze such image data to detect, e.g., street signs and/or landmarks such as buildings or sculptures, which may help to identify the location of a medical situation.

The above techniques for determining the target location associated with a medical situation are provided for illustrative purposes and not intended to be limiting. It should be understood that other techniques may be used to determine the target location, without departing from the scope of the invention.

B. Navigating the UAV to the Target Location

As noted above, method 600 involves a UAV navigating to the target location through the use of a navigation system and/or control system, among other possibilities. In particular, the target location may be determined before the UAV is dispatched. Further, a route to the target location may also be determined before the UAV is dispatched. A navigation module of the UAV, as discussed above, may further generate flight-control command according to the pre-determined route to the target location.

Further, in order to transport the medical device to the medical situation, a UAV may include a housing with a compartment and/or other features to hold the medical device during flight. A UAV may include different types of housings to transport a medical-support device to the target location. The type of housing used may depend on the size and shape of the medical-support device, in addition to the type of environment required by the medical-support device.

The size and shape of housing available to transport medical-support devices may vary based on the type of medical-support device. In an example embodiment, a medical-support device that is large and/or bulky, as compared to the size of the UAV, may be more easily transported by carrying the device outside the body of a UAV. Alternatively, a medical-support device that is small, as compared to the size of the UAV, may be transported more easily in an internal compartment.

For example, as discussed above and in FIG. 1, a UAV 100 may include a compartment 135, in which a medical-support device may be situated. The compartment may completely enclose the medical-support device. It may be shaped in order to appropriately house the medical-support device such that it is insulated and protected from outside elements.

The compartment may include protective materials to help protect the device, such as, but not limited to, Styrofoam insulation, foam insulation, packing "peanuts," or other types of padding material. This may be useful, for example, to transport items that are delicate or breakable, for instance. Examples of medical-support devices that may be delicate include, but are not limited to, mobile devices, head-mountable displays, or tablets.

In some embodiments, a medical-support device that requires a temperature-controlled environment may need to be transported in a temperature-controlled compartment. In such an embodiment, a UAV may include heating and/or cooling systems in order to control the temperature of a compartment. For example, electronic devices, such as HMDs or mobile devices, often have an operating temperature that includes a range of temperatures at which the electronic device can function properly. If an electronic device is exposed to a temperature outside of their operating temperature, the electronic device may overheat or freeze, thus damaging the electronic device or rendering it unusable. Additionally, some medicine, such as an epinephrine injection or dose of insulin, must remain at the correct temperature or within a certain temperature range in order to remain effective. Thus, due to the change in temperature at various flying heights or destination or heat emitted from the UAV, a temperature controlled transportation method for such medical-support devices is advantageous.

Further, the medical-support device may benefit from a housing that provides a power source. For example, a defibrillator may need to remain charged during flight in order to ensure that the device functions properly once it arrives at the medical situation. Thus, the UAV may provide a power source such that the medical-support device may be connected and charged throughout the flight.

C. Making a Determination that the UAV has Reached the Target Location

As noted above, block 606 of method 600 involves making a determination that the UAV has reached and is located at the target location of the medical situation. In particular, the UAV may detect when it has reached and is located at the target location of the medical situation. Alternatively, a remote device may recognize when the UAV has reached the target location.

At block 606, a UAV may use various techniques to determine that it is located at the target location. For example, if the target location is the GPS coordinates of the remote device from which the medical situation was reported, then a UAV 400 may use its GPS system 406 to determine when it has reached those GPS coordinates. Alternatively, the UAV may consider itself to have reached the target location when it is within a certain distance from the GPS coordinates (e.g., within 100 feet).

As another example, if the target location is a particular landmark (e.g., a particular building, a stadium, a park, or a certain beach), then a UAV 400 may utilize its GPS system 406 and/or another location-determination system in conjunction with mapping data to determine when the UAV is located at or near a location that the mapping data associates with the particular landmark. Such mapping data may be included in the data storage of a UAV, or may be provided to a UAV by a remote mapping server.

In some embodiments, the UAV may use a beacon-sensing localization process in order to determine that it has reached the target location. For example, beacon-sensing localization may involve the UAV searching for various types of directional signals that can be emitted by a remote device at the scene of a medical situation. Thus, when the beacon-sensor is sensed, the UAV may determine that it has reached the target location. The strength of the beacon-sensor may provide the UAV with further information regarding the target location. For example, a strengthening signal may indicate that the target location is approaching. A decreasing signal may represent that the UAV is moving away from the target location. Other examples are also possible.

D. Delivering the Medical-Support Device at the Location of the Medical Situation Block 608 of method 600 may involve a UAV causing a delivery mechanism to deliver a medical-support device at the target location in response to the determination that the UAV is located at the target location of the medical situation. In particular, the delivery mechanism may deliver the medical-support device to an individual in need of medical support, or assisting with medical support, at the target location where the medical situation is occurring.

i. Types of Medical-Support Devices

At block 608, a UAV may transport medical-support devices that are designed for a number of different medical situations, which, as discussed above, may be associated in some way. In particular, the medical-support device may provide medical support based on what type of emergency situation is occurring at the location of the medical situation. For example, a UAV may deliver a dive-accident device, which may include a flotation device, to a diver on the surface of the water who is in need of flotation assistance.

Such medical-support devices may include, as examples, but are not limited to: (a) medicines, such as a dose of insulin, (b) diagnostic devices, such as a pulse oximeter, blood pressure sensor, or EKG sensor, (c) treatment devices, such as an epinephrine injection, a first aid kit, a defibrillator, and/or (d) remote support devices, such as a mobile phone or a head-mountable device (HMD), among other possibilities.

In one embodiment, as discussed above, a UAV may be equipped with a standalone defibrillator for the treatment of cardiac arrest. In particular, the UAV may deliver an automated external defibrillator, known as an AED, which is capable of automatically detecting, diagnosing, and treating the shockable heart rhythms, such that a bystander at the location of a medical situation may use the defibrillator to resuscitate an individual in need. The defibrillator may be housed in a compartment located on the UAV or carried outside the body of the UAV. Other methods of storing the defibrillator may be possible as well.

In another embodiment, the AED may not require removal from the UAV prior to use. In particular, the UAV might itself function as a defibrillator. In such embodiments, components of the AED may be built into the body of the UAV, including the AED machine and its retractable electrode pads for administering shock to a person who is experiencing a cardiac event or arrest. Thus, a bystander located at the location of the medical-situation would not have to remove the medical-support device from the UAV and administration of treatment could occur immediately.

In one embodiment, when a UAV delivers an AED to a location of the medical situation, a bystander, who might be a layperson, may remove the AED from the UAV and apply treatment to the person in need. The UAV may also provide instructions for use of the AED. These instructions may be delivered in the form of written instructions, for example in a pamphlet or on a tablet or laptop computer.

In particular, the UAV may include a mobile device, tablet, laptop, or other electronic device to provide instructions on use of the defibrillator and treatment of the cardiac event or arrest. These instructions may be provided, for example, as textual/graphic instructions or audio/visual instructions. For example, the mobile device, tablet, or laptop may be delivered along with the defibrillator. The bystander located at the medical situation may remove the mobile device, tablet, or laptop and be instructed on how to begin administration of the treatment using the defibrillator. These devices may also allow for communication with a remote device, where medical personnel may be available to assist with the treatment.

In another embodiment, the UAV may deliver a head-mounted display that is pre-loaded with or otherwise able to provide video instructions along with the medical-support device to the bystander located at the medical situation. The HMD may provide textual, audio, or visual instructions on how to provide treatment using the medical-support device. For example, the HMD may provide a video tutorial describing how perform cardiopulmonary resuscitation (CPR), including instructions such as where to place the retractable electrode pads for administration a shock and how to begin the process. Further, the HMD may be capable of wirelessly connecting to a network in order to receive instructions based on the type of medical situation occurring.

In yet another example, the HMD may use augmented reality technology to provide medical assistance. For example, instructions for performing a medical procedure on an individual may be overlaid on the body of the person in need or projected onto a surface near the person in need. In one embodiment, these instructions may illustrate where to push on an individual's chest in order to properly perform CPR. In another embodiment, the instructions may include a visual overlay that illustrates where to attach AED electrodes. Other examples of instructions using augmented reality technology may exist as well. Additionally, these instructions may be projected by the use of a head-mounted display. In another embodiment, the UAV itself may project the instructions.

Further, the medical-support devices may be equipped with tele-medicine technology such that the devices can communicate with a remote location to transmit and receive audio and visual information. More specifically, the tele-medicine technology may aid in helping a remote operator diagnose the individual in need of assistance in order to properly provide aid to the scene. Thus, in one embodiment, the medical-support device may include a physical mechanism for providing audio and video information from the location of the medical situation to a remote location where medical personnel are available to provide assistance. Further, the medical-support device may also be equipped with a physical mechanism that is capable of receiving audio and video information. Such physical mechanisms may include, but are not limited to, speakers, microphones, cameras, projectors, and video displays.

In one example, a bystander equipped with an HMD may engage in a live session with a remote operator using a camera or microphone/speaker located on the HMD. This technology may allow for diagnostic tele-medicine to occur, such that a remote operator can properly diagnose the condition of the individual in need, and provide the appropriate assistance. For example, the remote operator may witness the medical condition of the individual in need through the camera or microphone on the HMD that the bystander is wearing. Thus, the remote operator may be able to diagnose the medical condition and provide instructions for assistance of the individual. More details concerning possible HMDs are provided in section IV.

Further, the medical-support devices described above may be capable of transmitting information locally or via WiFi or Bluetooth. For example, medical-support devices, such as a pulse oximeter or HMD, may transmit information regarding its diagnostic results to the UAV. In this embodiment, the UAV may act as a hub for long-range communication back to a remote location where medical personnel are available to provide medical support. This information may also be transmitted to a database where it is stored and may be reviewed at a later time, or back to the general Internet.

In an alternative embodiment, the UAV itself may act as the medical-support device and contain built-in equipment for providing medical support. For example, the UAV may include equipment capable of inputting and outputting video and audio information. In one embodiment, the UAV may include microphones, speakers and/or a camera such that audio and live video feed may be transmitted to a remote location. Medical-support personnel at the remote location may then receive the information from the scene of the medical situation and respond accordingly. As described above, the UAV may be equipped with augmented reality technology such that instructions can be projected onto a surface of onto the body of an individual in need of medical assistance.

Alternatively, the medical-support device may be built into the body of the UAV. For example, the UAV may deliver the device by landing, disable its rotors, and enter a mode where it acts as the medical-support device, such as an automated external defibrillator.

The determination of which medical-support device to deliver may be pre-determined or determined at the time of the medical emergency. For example, when an indication of a medical situation is received, such as a dive-accident, the medical-support device may be pre-determined based on the fact that the emergency is related to diving, therefore the medical-support device may be pre-determined to include a flotation device, an oxygen-therapy system, or a system for delivering visual and/or audible care instruction, such as for performing CPR.

In another embodiment, the selected medical-support device may be requested by individuals involved in the medical situation. For example, when an indication of a medical situation such as a car accident is received, a first aid kit may be pre-determined for delivery. Individuals at the scene, however, may note that the driver is suffering from an unrelated medical emergency, such as a diabetic attack, and thus request the delivery of a dose of insulin.

ii. Examples of Delivery Mechanisms

Once a UAV arrives at the scene of a medical situation, the UAV may need to deliver its medical device so that the device is usable to provide medical support. To do so, a UAV may include a delivery mechanism (or possibly multiple delivery mechanisms), which may be used at block 608 to deliver the medical device. Generally, a delivery mechanism may take the form of any system and/or functionality that can make a medical device available for use, once a UAV arrives at the location of a medical situation. Various types of delivery mechanisms are possible.

For example, in order to deliver a medical-support device that is housed in a compartment, the UAV may land at the location of the medical situation such that an individual at the scene may manually remove the medical-support device from the compartment. For example, as shown in FIG. 1, a compartment 135 may include a lid or closure in order to close the compartment and protect the medical-support device, which may be hinged so that a user can open it to access and/or remove a medical-support device. In another embodiment, a plastic or metal seal may be enclosing the compartment, such that the seal remains intact until an individual at the location of the medical situation breaks or removes the seal and opens the compartment. Other types of lids or tops are also possible. For instance, the compartment may be configured with a lid, which may be temporarily adhered to the remainder of the compartment using, for example, snap on or locking technology, magnetic force, or glue adhesion.

In another embodiment, the compartment may include a lock system that may be opened with the use of a code or key. The use of the lock system may guarantee that the proper recipient receives the medical-support device. In another embodiment, the compartments may be equipped with tamper-proof technology that would not only prevent unauthorized entry but also signal if unauthorized entry has been attempted. In another example, these compartments may be designed to destroy or permanently disable the contents if tampering occurs or if the device is removed illegitimately. Such tamper-proof or tamper-resistant technology can help to prevent unauthorized use from occurring. Such technology may particularly be useful for contents that are valuable or dangerous, such as medications that are prone to abusive use or tablet computers. Thus, if an intruder seeking to sell the contents obtains possession of the UAV, the compartment may disable the device, such as a mobile device, such that it is no longer useful or valuable.

Additionally or alternatively, the compartment may include a slide-out mechanism that allows the device to be released from the compartment. In one embodiment, the slide-out mechanism may be toggled once the UAV reaches the ground at the target location. In another embodiment, the individual at the target location may be able to manually release the slide-out mechanism by, for example, flipping a switch or pressing a release button.

In another example, the UAV may include a pick-and-place mechanism, which is capable of picking up and holding the device while the UAV is in flight. The device may be held at any location on the UAV, such as underneath the UAV or on top of the UAV, and then moved to a desired location and/or position once the UAV arrives at the location of the medical situation. For example, in order to hold the medical-support device underneath the UAV, a claw mechanism may be use to pick up and maintain control of the device during flight. In another embodiment, in order to carry the device on top of the UAV, a platform may be used on top of the UAV to maintain control of the device during flight.

In order to deliver the medical-support device that is being carried by a pick-and-place mechanism, the UAV may release the item once the UAV reaches the target location but while it is still airborne. In some implementations, the device may be placed on the ground. In other implementations, the device may be allowed to fall to the ground. In such circumstances, the device may be padded in order to protect it from any harm caused by the descent and landing. For example, the medical-support device may be protected by impact absorbing technology, such as bouncing air bags that cushion the fall. The bouncing air bags may continue to cushion the impact of the medical-support device and the ground until it comes to rest.

In some embodiments, the UAV may land at the target location, and the medical-support device may be automatically or manually released from the pick-and-place mechanism. In a further aspect, the medical-support device may only be physically released from the UAV or functionally enabled upon the detection of the presence of a certain device (e.g., a mobile device) through the use of a security system. For example, when a mobile device is used to call to report a medical situation, the medical-support system may provide the mobile device with a security key that may be transmitted in a signal. When the UAV then arrives at the medical situation, it may be capable of searching for the signal with the security key. If the UAV detects the signal from the cell phone that is transmitting the security key, then the UAV may physically release or functionally enable the medical-support device. This security system may also be applied to other methods of delivery and release of a medical-support device as discussed above.

In some embodiments, a parachute drop-system may be used to deliver a medical device. A parachute drop-system may be implemented on its own, or in conjunction with, e.g., a pick-and-place system, in order to reduce the speed at which the medical-support device falls and the resulting impact upon landing. The use of a parachute system for medical-device delivery may allow a UAV to remain airborne when it reaches the medical situation, which may allow for medical support at a location where landing the UAV is not be possible.

In one embodiment, a parachute may be attached to the medical-support device such that when the device is released from the UAV, a drag is created to slow down the device from falling down. In another embodiment, a parachute may also be attached to a container in which the medical-support device is enclosed. The container may be manually opened to access the device, or may be configured to automatically open or otherwise make the device available upon impact. Further, the container may include features to protect the device (e.g., padding or air bags that deploy upon the container impacting the ground).

In some embodiments, a winch system may be implemented to deliver medical-support devices. The winch system may enable the UAV the lower a medical-support device at a controlled rate using a winch line, such as a rope or cable. Thus, the UAV may hover in the air at a safe altitude where it is free from obstructions or obstacles that may hinder delivery of the medical-support devices. In an example embodiment, the winching system may include a safety release such that the UAV itself may not be pulled down if the medical-support device or winching line gets snagged or if an individual pulls on the line.

In some embodiments, a UAV's delivery mechanism may take the form of or include program instructions that are executable to position the UAV such that the device is available for use. For example, if the UAV houses an HMD in an open-top compartment, the delivery mechanism may simply be program instructions that are executable to position the UAV at a certain height, a certain distance from a person, and/or at a certain angle with respect to the person, such that the person can remove the HMD from the open-top compartment. Other examples are possible. Further, such program instructions may be implemented to position the HMD in a manner that facilitates the operation of a mechanical delivery mechanism, such as those described above.

Also as discussed above, control and delivery of the medical-support device may be controlled by a remote device, a UAV, or an individual located at the target location. In some embodiments, the UAV device may initiate the delivery of the medical-support device. In other embodiments, an individual or signal at the scene or located remotely may cause delivery to occur. Other examples may also be possible.

VI. EXAMPLE HEAD-MOUNTABLE DISPLAYS

Examples of HMDs that may be transported to a medical situation by a UAV according to an example embodiment, are described below.

An HMD may generally be any display device that is capable of being worn on the head and places a display in front of one or both eyes of the wearer. An HMD may take various forms such as a helmet or eyeglasses. As such, references to "eyeglasses" or a "glasses-style" HMD should be understood to refer to an HMD that has a glasses-like frame so that it can be worn on the head. Further, example embodiments may be implemented by or in association with an HMD with a single display or with two displays, which may be referred to as a "monocular" HMD or a "binocular" HMD, respectively.

Figure 7A:
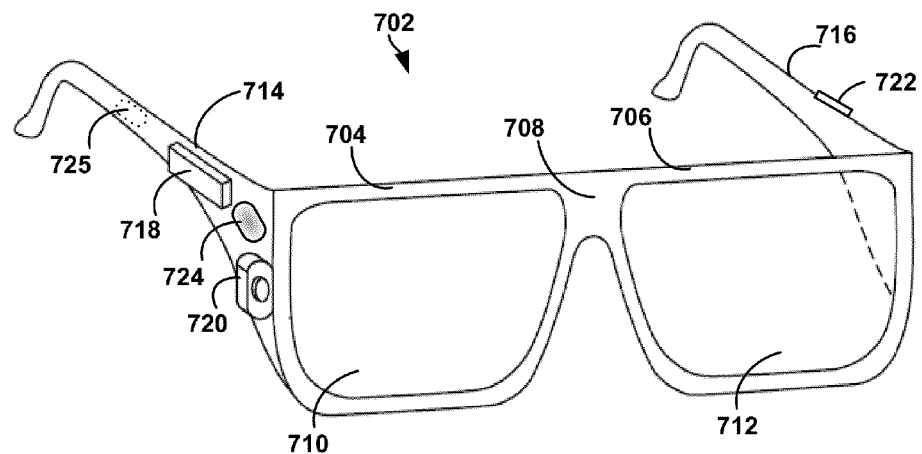
FIG. 7A illustrates a wearable computing system according to an example embodiment.

FIG. 7A illustrates a wearable computing system according to an example embodiment. In FIG. 7A, the wearable computing system takes the form of a head-mountable device (HMD) 702 (which may also be referred to as a head-mounted display). It should be understood, however, that example systems and devices may take the form of or be implemented within or in association with other types of devices, without departing from the scope of the invention. As illustrated in FIG. 7A, the HMD 702 includes frame elements including lens-frames 704, 706 and a center frame support 708, lens elements 710, 712, and extending side-arms 714, 716. The center frame support 708 and the extending side-arms 714, 716 are configured to secure the HMD 702 to a user's face via a user's nose and ears, respectively.

Each of the frame elements 704, 706, and 708 and the extending side-arms 714, 716 may be formed of a solid structure of plastic and/or metal, or may be formed of a hollow structure of similar material so as to allow wiring and component interconnects to be internally routed through the HMD 702. Other materials may be possible as well.

One or more of each of the lens elements 710, 712 may be formed of any material that can suitably display a projected image or graphic. Each of the lens elements 710, 712 may also be sufficiently transparent to allow a user to see through the lens element. Combining these two features of the lens elements may facilitate an augmented reality or heads-up display where the projected image or graphic is superimposed over a real-world view as perceived by the user through the lens elements.

The extending side-arms 714, 716 may each be projections that extend away from the lens-frames 704, 706, respectively, and may be positioned behind a user's ears to secure the HMD 702 to the user. The extending side-arms 714, 716 may further secure the HMD 702 to the user by extending around a rear portion of the user's head. Additionally or alternatively, for example, the HMD 702 may connect to or be affixed within a head-mounted helmet structure. Other configurations for an HMD are also possible.

The HMD 702 may also include an on-board computing system 718, an image capture device 720, a sensor 722, and a finger-operable touch pad 724. The on-board computing system 718 is shown to be positioned on the extending side-arm 714 of the HMD 702; however, the on-board computing system 718 may be provided on other parts of the HMD 702 or may be positioned remote from the HMD 702 (e.g., the on-board computing system 718 could be wire- or wirelessly-connected to the HMD 702). The on-board computing system 718 may include a processor and memory, for example. The on-board computing system 718 may be configured to receive and analyze data from the image capture device 720 and the finger-operable touch pad 724 (and possibly from other sensory devices, user interfaces, or both) and generate images for output by the lens elements 710 and 712.

The image capture device 720 may be, for example, a camera that is configured to capture still images and/or to capture video. In the illustrated configuration, image capture device 720 is positioned on the extending side-arm 714 of the HMD 702; however, the image capture device 720 may be provided on other parts of the HMD 702. The image capture device 720 may be configured to capture images at various resolutions or at different frame rates. Many image capture devices with a small form-factor, such as the cameras used in mobile phones or webcams, for example, may be incorporated into an example of the HMD 702.

Further, although FIG. 7A illustrates one image capture device 720, more image capture device may be used, and each may be configured to capture the same view, or to capture different views. For example, the image capture device 720 may be forward facing to capture at least a portion of the real-world view perceived by the user. This forward facing image captured by the image capture device 720 may then be used to generate an augmented reality where computer generated images appear to interact with or overlay the real-world view perceived by the user.

The sensor 722 is shown on the extending side-arm 716 of the HMD 702; however, the sensor 722 may be positioned on other parts of the HMD 702. For illustrative purposes, only one sensor 722 is shown. However, in an example embodiment, the HMD 702 may include multiple sensors. For example, an HMD 702 may include sensors 702 such as one or more gyroscopes, one or more accelerometers, one or more magnetometers, one or more light sensors, one or more infrared sensors, and/or one or more microphones. Other sensing devices may be included in addition or in the alternative to the sensors that are specifically identified herein.

The finger-operable touch pad 724 is shown on the extending side-arm 714 of the HMD 702. However, the finger-operable touch pad 724 may be positioned on other parts of the HMD 702. Also, more than one finger-operable touch pad may be present on the HMD 702. The finger-operable touch pad 724 may be used by a user to input commands. The finger-operable touch pad 724 may sense at least one of a pressure, position and/or a movement of one or more fingers via capacitive sensing, resistance sensing, or a surface acoustic wave process, among other possibilities. The finger-operable touch pad 724 may be capable of sensing movement of one or more fingers simultaneously, in addition to sensing movement in a direction parallel or planar to the pad surface, in a direction normal to the pad surface, or both, and may also be capable of sensing a level of pressure applied to the touch pad surface. In some embodiments, the finger-operable touch pad 724 may be formed of one or more translucent or transparent insulating layers and one or more translucent or transparent conducting layers. Edges of the finger-operable touch pad 724 may be formed to have a raised, indented, or roughened surface, so as to provide tactile feedback to a user when the user's finger reaches the edge, or other area, of the finger-operable touch pad 724. If more than one finger-operable touch pad is present, each finger-operable touch pad may be operated independently, and may provide a different function.

In a further aspect, HMD 702 may be configured to receive user input in various ways, in addition or in the alternative to user input received via finger-operable touch pad 724. For example, on-board computing system 718 may implement a speech-to-text process and utilize a syntax that maps certain spoken commands to certain actions. In addition, HMD 702 may include one or more microphones via which a wearer's speech may be captured. Configured as such, HMD 702 may be operable to detect spoken commands and carry out various computing functions that correspond to the spoken commands.

As another example, HMD 702 may interpret certain head-movements as user input. For example, when HMD 702 is worn, HMD 702 may use one or more gyroscopes and/or one or more accelerometers to detect head movement. The HMD 702 may then interpret certain head-movements as being user input, such as nodding, or looking up, down, left, or right. An HMD 702 could also pan or scroll through graphics in a display according to movement. Other types of actions may also be mapped to head movement.

As yet another example, HMD 702 may interpret certain gestures (e.g., by a wearer's hand or hands) as user input. For example, HMD 702 may capture hand movements by analyzing image data from image capture device 720, and initiate actions that are defined as corresponding to certain hand movements.

As a further example, HMD 702 may interpret eye movement as user input. In particular, HMD 702 may include one or more inward-facing image capture devices and/or one or more other inward-facing sensors (not shown) that may be used to track eye movements and/or determine the direction of a wearer's gaze. As such, certain eye movements may be mapped to certain actions. For example, certain actions may be defined as corresponding to movement of the eye in a certain direction, a blink, and/or a wink, among other possibilities.

HMD 702 also includes a speaker 725 for generating audio output. In one example, the speaker could be in the form of a bone conduction speaker, also referred to as a bone conduction transducer (BCT). Speaker 725 may be, for example, a vibration transducer or an electroacoustic transducer that produces sound in response to an electrical audio signal input. The frame of HMD 702 may be designed such that when a user wears HMD 702, the speaker 725 contacts the wearer. Alternatively, speaker 725 may be embedded within the frame of HMD 702 and positioned such that, when the HMD 702 is worn, speaker 725 vibrates a portion of the frame that contacts the wearer. In either case, HMD 702 may be configured to send an audio signal to speaker 725, so that vibration of the speaker may be directly or indirectly transferred to the bone structure of the wearer. When the vibrations travel through the bone structure to the bones in the middle ear of the wearer, the wearer can interpret the vibrations provided by BCT 725 as sounds.

Various types of bone-conduction transducers (BCTs) may be implemented, depending upon the particular implementation. Generally, any component that is arranged to vibrate the HMD 702 may be incorporated as a vibration transducer. Yet further it should be understood that an HMD 702 may include a single speaker 725 or multiple speakers. In addition, the location(s) of speaker(s) on the HMD may vary, depending upon the implementation. For example, a speaker may be located proximate to a wearer's temple (as shown), behind the wearer's ear, proximate to the wearer's nose, and/or at any other location where the speaker 725 can vibrate the wearer's bone structure.

Figure 7B:
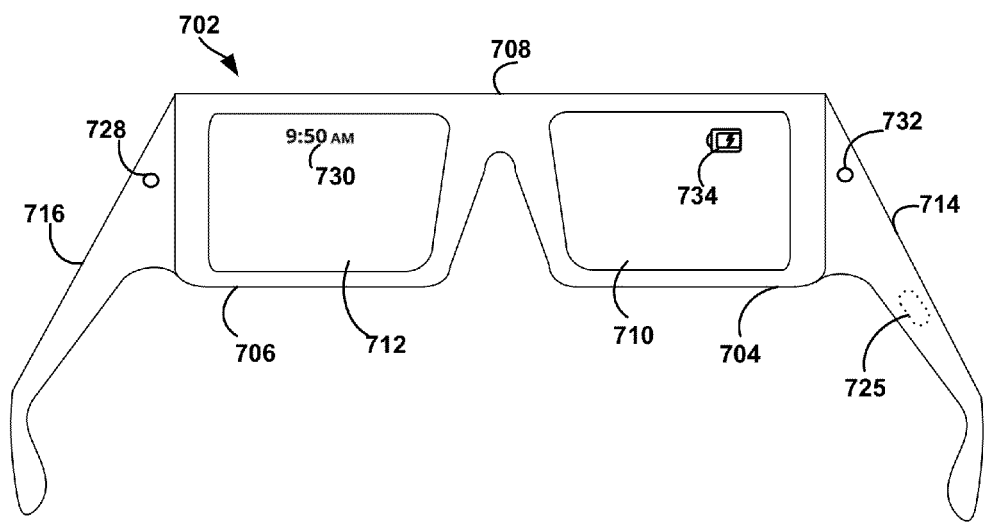
FIG. 7B illustrates an alternate view of the wearable computing system illustrated in FIG. 7A.

FIG. 7B illustrates an alternate view of the wearable computing device illustrated in FIG. 7A. As shown in FIG. 7B, the lens elements 710, 712 may act as display elements. The HMD 702 may include a first projector 728 coupled to an inside surface of the extending side-arm 716 and configured to project a display 730 onto an inside surface of the lens element 712. Additionally or alternatively, a second projector 732 may be coupled to an inside surface of the extending side-arm 714 and configured to project a display 734 onto an inside surface of the lens element 710.

The lens elements 710, 712 may act as a combiner in a light projection system and may include a coating that reflects the light projected onto them from the projectors 728, 732. In some embodiments, a reflective coating may not be used (e.g., when the projectors 728, 732 are scanning laser devices).

In alternative embodiments, other types of display elements may also be used. For example, the lens elements 710, 712 themselves may include: a transparent or semi-transparent matrix display, such as an electroluminescent display or a liquid crystal display, one or more waveguides for delivering an image to the user's eyes, or other optical elements capable of delivering an in focus near-to-eye image to the user. A corresponding display driver may be disposed within the frame elements 704, 706 for driving such a matrix display. Alternatively or additionally, a laser or LED source and scanning system could be used to draw a raster display directly onto the retina of one or more of the user's eyes. Other possibilities exist as well.

Figure 7C:
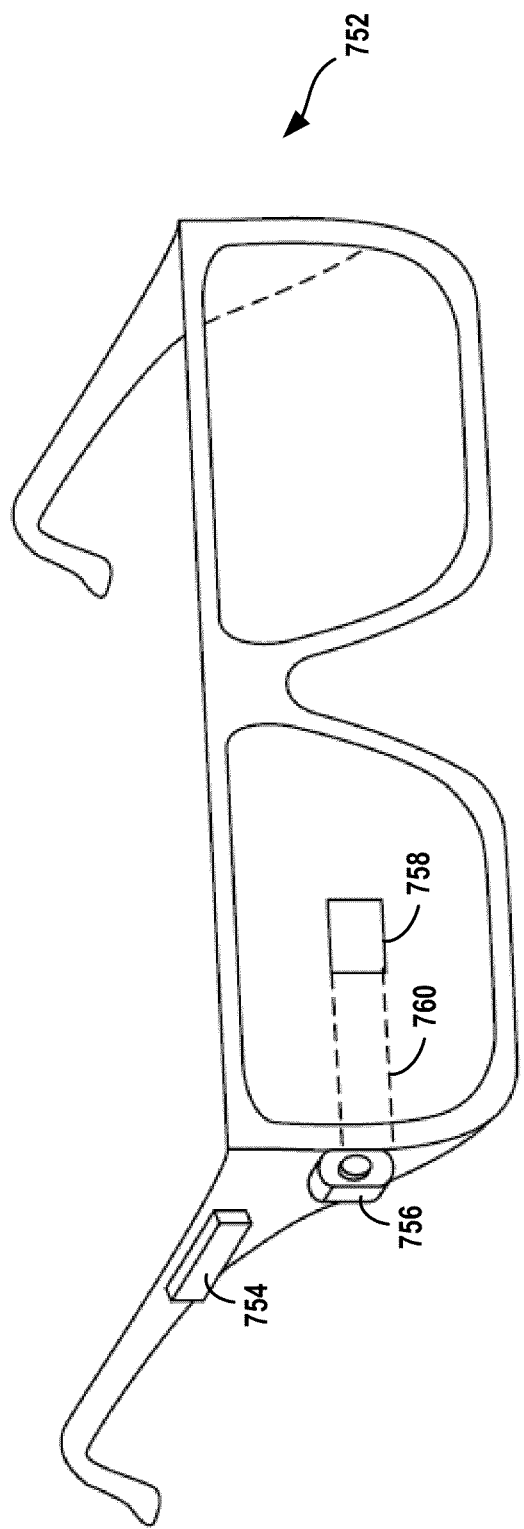
FIG. 7C illustrates another wearable computing system according to an example embodiment.

FIG. 7C illustrates another wearable computing system according to an example embodiment, which takes the form of an HMD 752. The HMD 752 may include frame elements and side-arms such as those described with respect to FIGS. 7A and 7B. The HMD 752 may additionally include an on-board computing system 754 and an image capture device 756, such as those described with respect to FIGS. 7A and 7B. The image capture device 756 is shown mounted on a frame of the HMD 752. However, the image capture device 756 may be mounted at other positions as well.

As shown in FIG. 7C, the HMD 752 may include a single display 758 which may be coupled to the device. The display 758 may be formed on one of the lens elements of the HMD 752, such as a lens element described with respect to FIGS. 7A and 7B, and may be configured to overlay computer-generated graphics in the user's view of the physical world. The display 758 is shown to be provided in a center of a lens of the HMD 752, however, the display 758 may be provided in other positions, such as for example towards either the upper or lower portions of the wearer's field of view. The display 758 is controllable via the computing system 754 that is coupled to the display 758 via an optical waveguide 760.

Figure 7D:
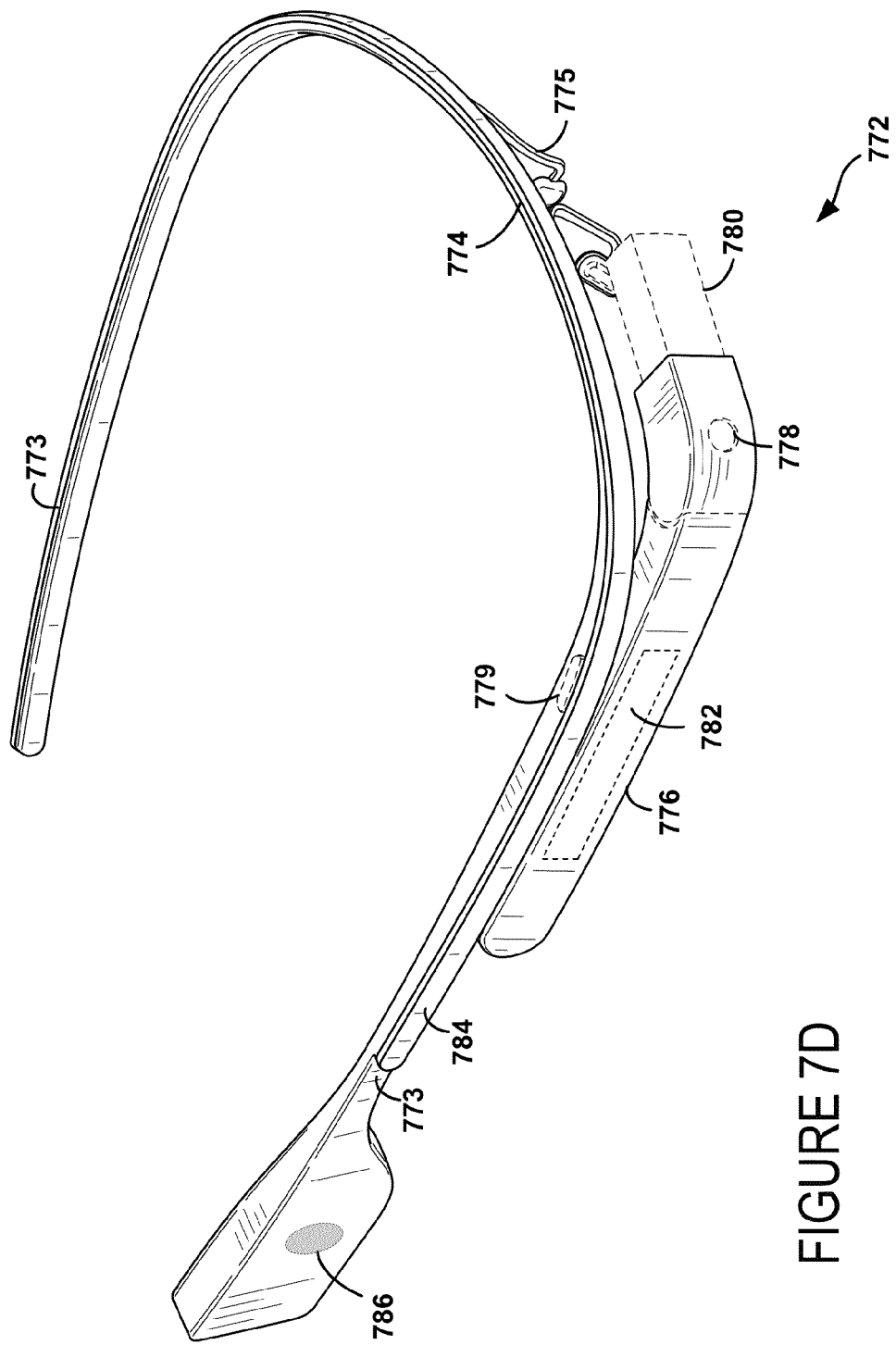
FIG. 7D illustrates another wearable computing system according to an example embodiment.

FIG. 7D illustrates another wearable computing system according to an example embodiment, which takes the form of a monocular HMD 772. The HMD 772 may include side-arms 773, a center frame support 774, and a bridge portion with nosepiece 775. In the example shown in FIG. 7D, the center frame support 774 connects the side-arms 773. The HMD 772 does not include lens-frames containing lens elements. The HMD 772 may additionally include a component housing 776, which may include an on-board computing system (not shown), an image capture device 778, and a button 779 for operating the image capture device 778 (and/or usable for other purposes). Component housing 776 may also include other electrical components and/or may be electrically connected to electrical components at other locations within or on the HMD. HMD 772 also includes a BCT 786.

The HMD 772 may include a single display 780, which may be coupled to one of the side-arms 773 via the component housing 776. In an example embodiment, the display 780 may be a see-through display, which is made of glass and/or another transparent or translucent material, such that the wearer can see their environment through the display 780. Further, the component housing 776 may include the light sources (not shown) for the display 780 and/or optical elements (not shown) to direct light from the light sources to the display 780. As such, display 780 may include optical features that direct light that is generated by such light sources towards the wearer's eye, when HMD 772 is being worn.

In a further aspect, HMD 772 may include a sliding feature 784, which may be used to adjust the length of the side-arms 773. Thus, sliding feature 784 may be used to adjust the fit of HMD 772. Further, an HMD may include other features that allow a wearer to adjust the fit of the HMD, without departing from the scope of the invention.

Figure 7E:
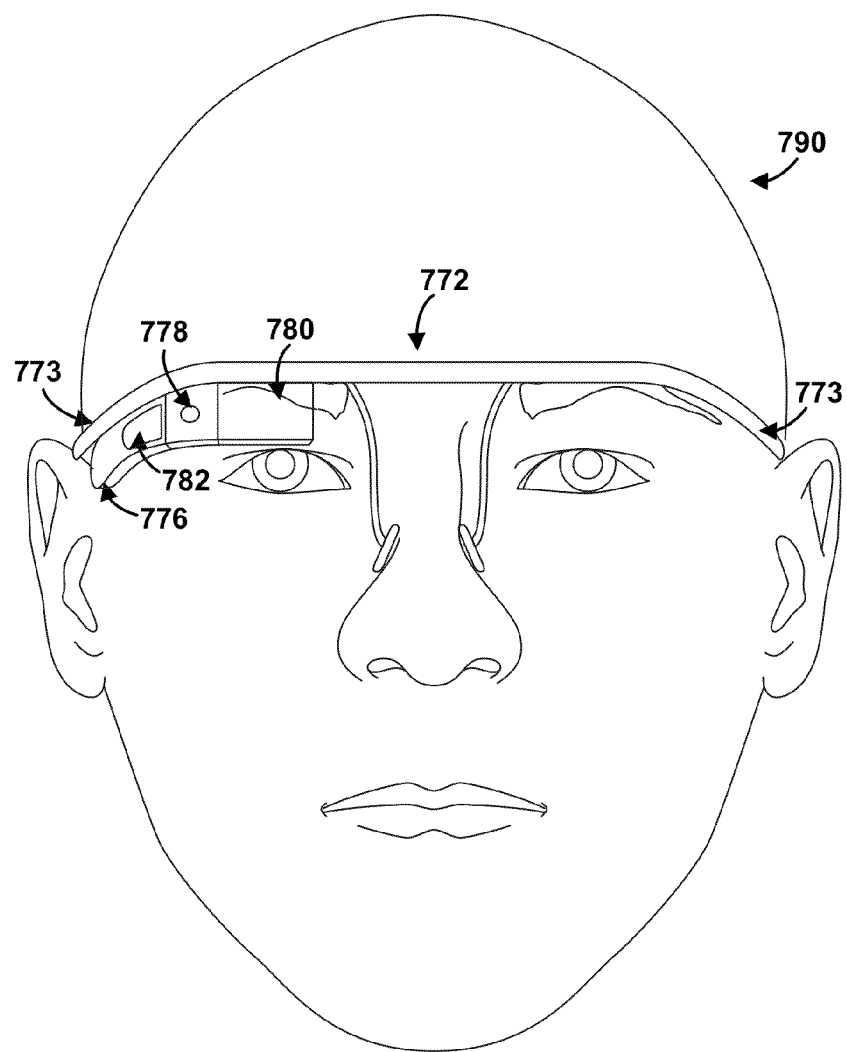
FIGS. 7E to 7G are simplified illustrations of the wearable computing system shown in FIG. 7D, being worn by a wearer.
Figure 7F:
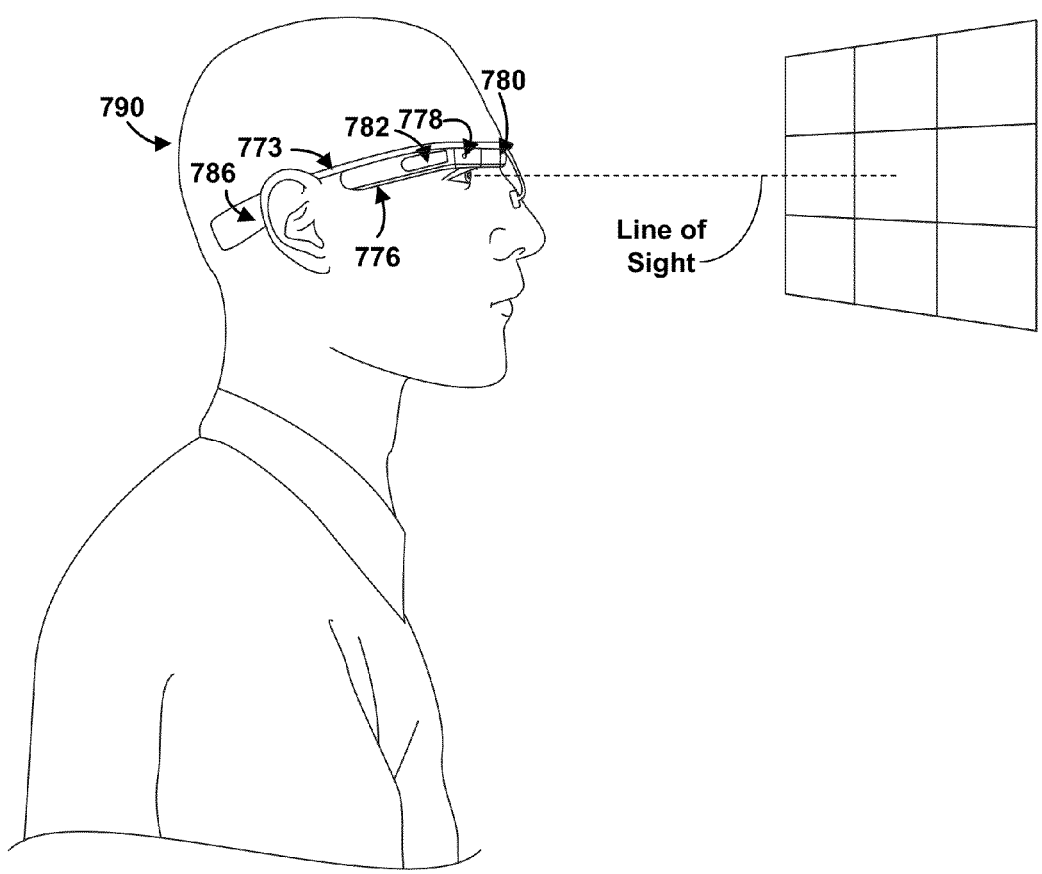
Figure 7G:
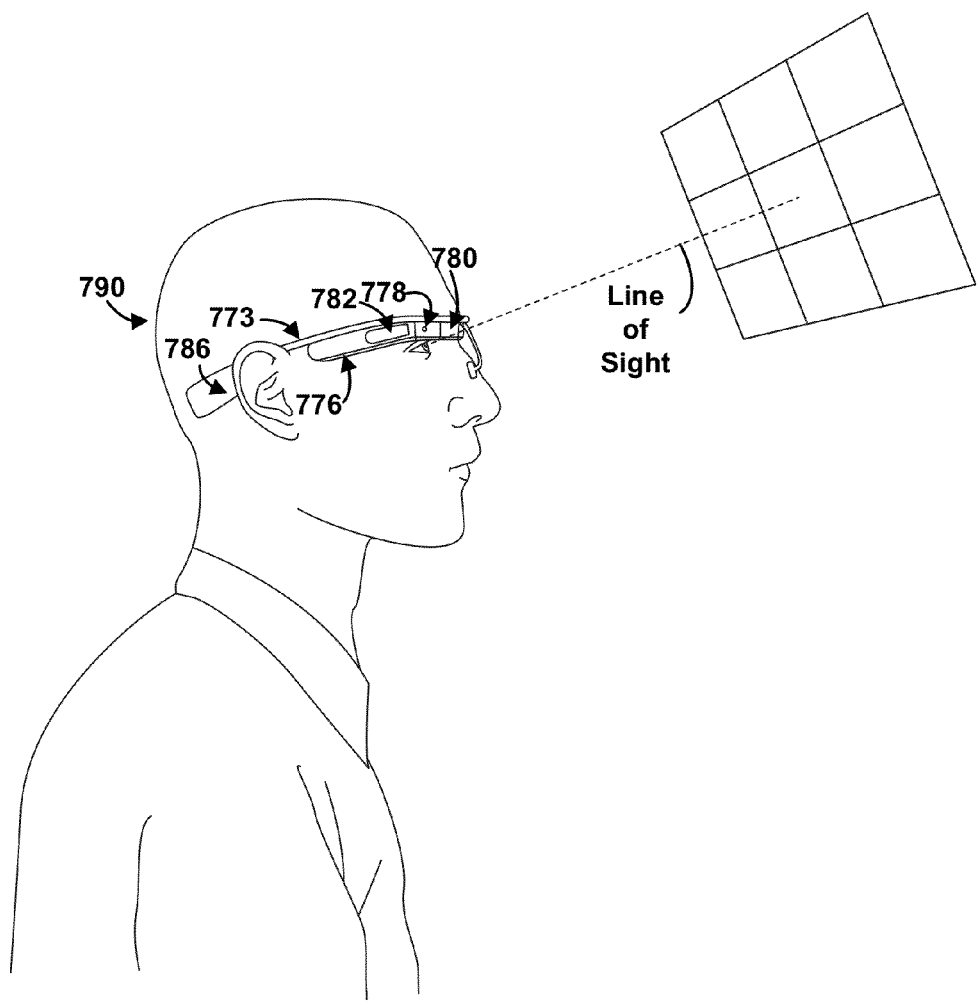

FIGS. 7E to 7G are simplified illustrations of the HMD 772 shown in FIG. 7D, being worn by a wearer 790. As shown in FIG. 7F, when HMD 772 is worn, BCT 786 is arranged such that when HMD 772 is worn, BCT 786 is located behind the wearer's ear. As such, BCT 786 is not visible from the perspective shown in FIG. 7E.

In the illustrated example, the display 780 may be arranged such that when HMD 772 is worn, display 780 is positioned in front of or proximate to a user's eye when the HMD 772 is worn by a user. For example, display 780 may be positioned below the center frame support and above the center of the wearer's eye, as shown in FIG. 7E. Further, in the illustrated configuration, display 780 may be offset from the center of the wearer's eye (e.g., so that the center of display 780 is positioned to the right and above of the center of the wearer's eye, from the wearer's perspective).

Configured as shown in FIGS. 7E to 7G, display 780 may be located in the periphery of the field of view of the wearer 790, when HMD 772 is worn. Thus, as shown by FIG. 7F, when the wearer 790 looks forward, the wearer 790 may see the display 780 with their peripheral vision. As a result, display 780 may be outside the central portion of the wearer's field of view when their eye is facing forward, as it commonly is for many day-to-day activities. Such positioning can facilitate unobstructed eye-to-eye conversations with others, as well as generally providing unobstructed viewing and perception of the world within the central portion of the wearer's field of view. Further, when the display 780 is located as shown, the wearer 790 may view the display 780 by, e.g., looking up with their eyes only (possibly without moving their head). This is illustrated as shown in FIG. 7G, where the wearer has moved their eyes to look up and align their line of sight with display 780. A wearer might also use the display by tilting their head down and aligning their eye with the display 780.

Figure 8A:
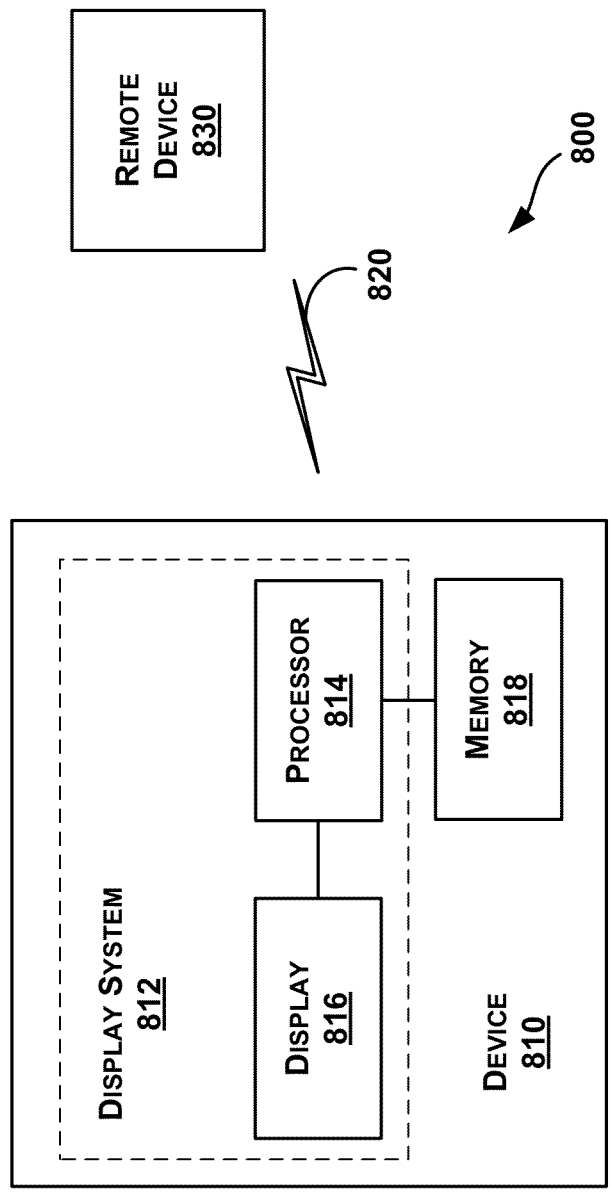
FIG. 8A illustrates a schematic drawing of a computing device according to an example embodiment.
Figure 8B:
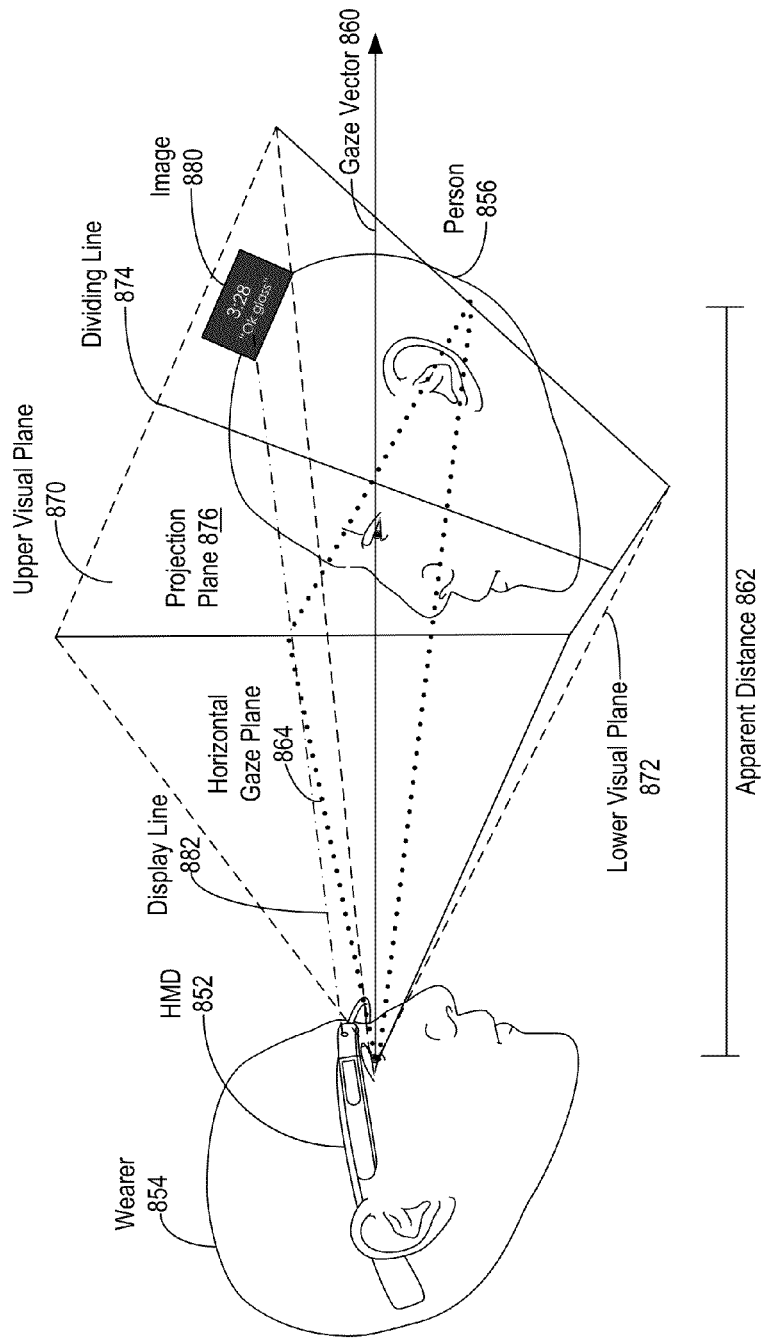
FIG. 8B shows an example projection of an image by an example head-mountable device (HMD), according to an example embodiment.

FIG. 8A is a simplified block diagram a computing device 810 according to an example embodiment. In an example embodiment, device 810 communicates using a communication link 820 (e.g., a wired or wireless connection) to a remote device 830. The device 810 may be any type of device that can receive data and display information corresponding to or associated with the data. For example, the device 810 may be a heads-up display system, such as the head-mounted devices 702, 752, or 772 described with reference to FIGS. 7A to 7G.

Thus, the device 810 may include a display system 812 comprising a processor 814 and a display 816. The display 810 may be, for example, an optical see-through display, an optical see-around display, or a video see-through display. The processor 814 may receive data from the remote device 830, and configure the data for display on the display 816. The processor 814 may be any type of processor, such as a microprocessor or a digital signal processor, for example.

The device 810 may further include on-board data storage, such as memory 818 coupled to the processor 814. The memory 818 may store software that can be accessed and executed by the processor 814, for example.

The remote device 830 may be any type of computing device or transmitter including a laptop computer, a mobile telephone, or tablet computing device, etc., that is configured to transmit data to the device 810. The remote device 830 and the device 810 may contain hardware to enable the communication link 820, such as processors, transmitters, receivers, antennas, etc.

Further, remote device 830 may take the form of or be implemented in a computing system that is in communication with and configured to perform functions on behalf of client device, such as computing device 810. Such a remote device 830 may receive data from another computing device 810 (e.g., an HMD 702, 752, or 772 or a mobile phone), perform certain processing functions on behalf of the device 810, and then send the resulting data back to device 810. This functionality may be referred to as "cloud" computing.

In FIG. 8A, the communication link 820 is illustrated as a wireless connection; however, wired connections may also be used. For example, the communication link 820 may be a wired serial bus such as a universal serial bus or a parallel bus. A wired connection may be a proprietary connection as well. The communication link 820 may also be a wireless connection using, e.g., Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities. The remote device 830 may be accessible via the Internet and may include a computing cluster associated with a particular web service (e.g., social-networking, photo sharing, address book, etc.).

VII. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

We claim:

1. An unmanned aerial vehicle (UAV) comprising:
   a housing that is configured to hold a medical-support device;
   a delivery mechanism, wherein the delivery mechanism comprises a winch system that is configured to deliver the medical-support device to a target location associated with an individual in need of medical assistance; and a control system, wherein said control system is configured to:
receive a request for assistance at an individual medical situation, wherein the request comprises location data corresponding to the target location;
determine the target location based on the location data;
navigate the UAV from a remote location to the target location, wherein the UAV navigates to the target location in a forward-flight mode;
make a determination that the UAV is located at or near to the target location;
in response to the determination that the UAV is located at or near to the target location, transition the UAV into a hover flight mode; and
cause the winch system to deliver the medical-support device to the target location by lowering the medical-support device towards a ground, such that the medical-support device is provided for medical assistance to the individual in need of medical assistance.

2. The UAV of claim 1, wherein the medical-support device is configured to provide instructions for medical treatment.

3. The UAV of claim 2, wherein the instructions for medical treatment are pre-loaded.

4. The UAV of claim 2, wherein the instructions for medical treatment are in the form of audio or visual instructions.

5. The UAV of claim 1, wherein the medical-support device comprises a head-mountable device (HMD).

6. The UAV of claim 1, wherein the medical-support device is at least one of a medicine, a diagnostic device, a treatment device, a remote support device, a pulse oximeter, a blood pressure sensor, an EKG sensor, an epinephrine injection, or a first aid kit.

7. The UAV of claim 1, wherein the medical-support device is a defibrillator.

8. The UAV of claim 1, wherein the medical-support device is at least one of a mobile phone, a tablet computer, or a laptop computer.

9. The UAV of claim 1, wherein the winch system comprises a compartment from which the medical-support device is manually removable.

10. The UAV of claim 9, wherein the compartment comprises a sliding system to slide the medical-support device out of the compartment.

11. The UAV of claim 1, wherein the location data is comprised of Global Position System (GPS) coordinates.

12. The UAV of claim 1, wherein the request for assistance at the individual medical situation is received from a mobile device.

13. A method comprising:
housing, by a housing system of an unmanned aerial vehicle (UAV), a medical-support device;
receiving, by a computing system of the UAV, a request for assistance at an individual medical situation, wherein the request comprises location data corresponding to a target location;
determining, by the computing system of the UAV, the target location, wherein the target location is associated with an individual in need of medical assistance;
navigating, by the computing system of the UAV, the UAV from a remote location to the target location, wherein the UAV navigates to the target location in a forward-flight mode;
making, by the computing system of the UAV, a determination that the UAV is located at or near to the target location;
in response to the determination that the UAV is located at or near to the target location, transitioning the UAV into a hover flight mode; and
delivering, by a delivery mechanism, the medical-support device to the target location by lowering the medical-support device towards to a ground, such that the medical-support device is provided for medical assistance to the individual in need of medical assistance, wherein the delivery mechanism comprises a winch system.

14. The method of claim 13, wherein the medical-support device comprises a head-mountable device (HMD).

15. The method of claim 13, wherein the winch system comprises a compartment wherein the medical-support device may be manually removed from the housing.

16. The method of claim 15, wherein the compartment comprises a sliding system to slide the medical-support device out of the housing.

17. The method of claim 13, wherein the medical-support device is configured to provide instructions for medical treatment.

18. The method of claim 17, wherein the instructions for medical treatment are pre-loaded.

19. The method of claim 17, wherein the instructions for medical treatment are in the form of audio or visual instructions.

20. A non-transitory computer readable medium having stored therein instructions that are executable to cause a computing device to perform functions comprising:
receiving a request for assistance at an individual medical situation, wherein the request comprises location data corresponding to a target location;
determining the target location, wherein the target location is associated with an individual in need of medical assistance;
using a navigation system to navigate an unmanned aerial vehicle (UAV) from a remote location to the target location, wherein the UAV navigates to the target location in a forward-flight mode;
making a determination that the UAV is located at or near to the target location;
in response to the determination that the UAV is located at or near to the target location, transitioning the UAV into a hover flight mode; and
using a delivery mechanism to deliver the medical-support device to the target location by lowering the medical-support device towards a ground, such that the medical support device is provided for medical assistance to the individual in need of medical assistance, wherein the delivery mechanism comprises a winch system.

21. The non-transitory computer readable medium of claim 20, wherein the medical-support device is a defibrillator.

22. The non-transitory computer readable medium of claim 20, wherein the medical-support device comprises a head-mountable device (HMD).

23. The non-transitory computer readable medium of claim 20, wherein the medical-support device is configured to provide instructions for medical treatment.

24. The non-transitory computer readable medium of claim 23, wherein the instructions for medical treatment are pre-loaded.

25. The non-transitory computer readable medium of claim 23, wherein the instructions for medical treatment are in the form of audio or visual instructions.

* * * * *

UNITED STATES PATENT AND TRADEMARK OFFICE
CERTIFICATE OF CORRECTION

| | |
|---|---|
| PATENT NO. | : 8,948,935 B1 |
| APPLICATION NO. | : 13/732958 |
| DATED | : February 3, 2015 |
| INVENTOR(S) | : Eric Peeters et al. |

It is certified that error appears in the above-identified patent and that said Letters Patent is hereby corrected as shown below:

In the Claims

In Claim 13, Column 36, at line 9, following the word "towards" please delete the word "to".

Signed and Sealed this
Twelfth Day of May, 2015

Michelle K. Lee
*Director of the United States Patent and Trademark Office*